United States Patent [19]
Nantz et al.

[11] Patent Number: 5,925,623
[45] Date of Patent: Jul. 20, 1999

[54] FORMULATIONS AND METHODS FOR GENERATING ACTIVE CYTOFECTIN:POLYNUCLEOTIDE TRANSFECTION COMPLEXES

[75] Inventors: Michael H. Nantz; Michael J. Bennett, both of Davis, Calif.; Rajiv P. Balasubramaniam, Rochester, N.Y.; Alfred M. Aberle, Vallejo; Robert W. Malone, Davis, both of Calif.

[73] Assignee: The Regents of the University of California, Oakland, Calif.

[21] Appl. No.: 08/679,971

[22] Filed: Jul. 15, 1996

Related U.S. Application Data

[63] Continuation-in-part of application No. 08/534,471, Sep. 27, 1995.

[51] Int. Cl.$^6$ .................................................. A01N 43/04
[52] U.S. Cl. ......................... 514/44; 435/69.1; 436/501; 935/77; 935/78
[58] Field of Search ........................ 435/69.1; 436/501; 514/44; 536/22.1, 23.1, 24.1, 24.5, 33; 935/77, 78

[56] References Cited

U.S. PATENT DOCUMENTS

| | | | |
|---|---|---|---|
| 4,812,449 | 3/1989 | Rideout | 514/183 |
| 5,171,678 | 12/1992 | Behr et al. | 435/172.3 |
| 5,186,923 | 2/1993 | Piwnica-Worms et al. | 424/9 |
| 5,208,036 | 5/1993 | Eppstein et al. | 424/450 |
| 5,264,618 | 11/1993 | Felgner et al. | 560/224 |
| 5,277,897 | 1/1994 | Piwnica-Worms et al. | 424/1.65 |
| 5,279,833 | 1/1994 | Rose | 424/450 |
| 5,334,761 | 8/1994 | Gebeyehu et al. | 564/197 |

FOREIGN PATENT DOCUMENTS

| | | |
|---|---|---|
| 9514651 | 6/1995 | WIPO . |

OTHER PUBLICATIONS

A Flexible Approach to Synthetic Lipid Ammonium Salts for Polynucleotide Transfection by Bennett et al., Tetrahedron Letters, vol. 36, No. 13, pp. 2207–2210, 1995.

The counterion influence on cationic lipid–mediated transfection of plasmid DNA by Aberle et al., BBA, 1299, pp. 281–283, 1996.

Mayer et al. (1986) Biochimica et Biophysica Acta, vol. 858, pp. 161–168.

Abramson et al. (1964) The Journal of Biological Chemistry, vol. 239, No. 1, pp. 70–76.

*Primary Examiner*—Ardin H. Marschel
*Attorney, Agent, or Firm*—James M. Ritchey

[57] ABSTRACT

In the generation of cytofectin:polynucleotide complexes for transfection of cells, formulations, counterions, and reaction conditions for maximizing the transfection include using a cationic amine compound that has the general structure:

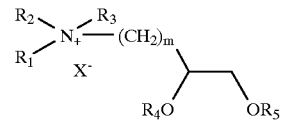

wherein $R_4$ and $R_5$ are a pair of same or different lipoyl moieties selected from a group consisting of an alkyl, alkenyl, alkynyl, alkanoyl, alkenoyl, or alkynoyl groups and for $R_1$, $R_2$, and $R_3$ at least two are hydroxylated, ether containing, or acyloxy containing alkyl, alkenyl, or alkynyl groups or at least one amine bonded halogen containing moiety selected from a group consisting of a halogenated alkyl, alkenyl, or alkynyl group or a mixture of at least one halogen containing moiety selected from a group consisting of a halogenated alkyl, alkenyl, or alkynyl group and at least one hydroxylated, ether containing, or acyloxy containing alkyl, alkenyl, or alkynyl group, and $X^-$ is an oxyanion or halide counterion.

5 Claims, 9 Drawing Sheets

A.

DMTAP        DMEAP        DMPAP

Increase in cross-sectional area of polar domain →

B.

DMPAP        DMMEP        DMRI

Increase in available hydrogen bonding modes →

C

DMPAP        DMRI        DMFEP

Increase in inductive influence on charged center →

$R = -(CH_2)_{12}CH_3)$

FORMULATIONS AND METHODS FOR GENERATING ACTIVE CYTOFECTIN: POLYNUCLEOTIDE TRANSFECTION COMPLEXES

This is a continuation-in-part of U.S. Ser. No. 08/534,471; filed Sep. 27, 1995.

BACKGROUND OF THE INVENTION

1. Field of the Invention

Provided are formulations and methods of producing active cytofectin:polynucleotide transfection complexes from a collection of cytofectins (cytofectins are defined as chemical species that are cationic transfection amphiphiles) or cationic lipids that bind and transport polynucleotides through membrane barriers. More specifically, structural features in cytofectins that improve transfection are selected, cytofectin counterions that improve transfection are chosen, and heating/sonication conditions for the formation of transfectin:polynucleotide complexes are maximized.

2. Description of the Background Art

Cellular transfection strategies for gene therapy and similar goals have been designed and performed, but many of these procedures involve recombinant virus vectors and various problems exist with these viral gene transfer systems. Even generally advantageous adenovirus techniques encounter difficulties since most humans have antibodies to many of the adenovirus serogroups, including those that have been chosen as vectors. Wild type adenoviral superinfection of an adenoviral vector treated patient may result in propagating the recombinant vector as a defective viral particle, with the ability to infect many unintended individuals (if chosen to have a rare serogroup). The chance of adenoviral contamination is quite low but not impossible. The safety of using these genetic materials in humans remains unclear and thus hazardous.

Unfortunately, the potential of gene transfer-based research to improve human health will be restricted unless improved methods are developed for in vivo delivery of foreign genetic material into cells and tissues. Currently used viral and non-viral transfection reagents have been compromised by one or more problems pertaining to: 1) associated health risks, 2) immunological complications, 3) inefficient in vivo transfection efficiency, and 4) direct cytotoxicity. The development of safe and effective polynucleotide-based medicines will require improved solutions which address these problems. Therefore, safe, non-viral vector methods for transfection or gene therapy are essential.

Cationic amphiphiles are currently regarded as an alternative to viral vector technology for in vivo polynucleotide delivery. Cationic lipid-based reagents avoid many of the health and immunological concerns associated with viral vectors. In a practical sense, cationic amphiphile-based delivery agents are relatively simple to use, and offer unparalleled flexibility in the nature of the material that can be delivered. Typically, cationic lipid complexes are prepared by mixing the cationic lipid (cytofectin) with the desired DNA (1), RNA (2), antisense oligomer (3), or protein (4) to yield active particles; in contrast to the laborious recombinant DNA and cell culture manipulations which are typically required to produce virus-derived delivery agents.

A few such lipid delivery systems for transporting DNA, proteins, and other chemical materials across membrane boundaries have been synthesized by research groups and business entities. Most of the synthesis schemes are relatively complex and generate lipid based delivery systems having only limited transfection abilities. A need exists in the field of gene therapy for cationic lipid species that have a high biopolymer transport efficiency. It has been known for some time that a very limited number of certain quaternary ammonium derivatized (cationic) liposomes spontaneously associate with DNA, fuse with cell membranes, and deliver the DNA into the cytoplasm (as noted above, these species have been termed "cytofectins"). LIPOFECTIN™ represents a first generation of cationic liposome formulation development. LIPOFECTIN™ is composed of a 1:1 formulation of the quaternary ammonium containing compound DOTMA and dioleoylphosphatidylethanolamine sonicated into small unilamellar vesicles in water. Problems associated with LIPOCFECTIN™ include non-metabolizable ether bonds, inhibition of protein kinase C activity, and direct cytotoxicity. In response to these problems, a number of other related compounds have been developed. The monoammonium compounds of the subject invention improve upon the capabilities of existing cationic liposomes and serve as a very efficient delivery system for biologically active chemicals.

Since the original report (Felgner, P. L., Gadek, T. R., Holm, M., Roman, R., Chan, H. W., Wenz, M., Northrop, J. P., Ringold, G. M. and Danielsen, M. 1987. Lipofection: a highly efficient, lipid-mediated DNA-transfection procedure. Proc. Natl. Acad. Sci. U.S.A. 84(21): 7413–7, which is herein incorporated by reference, as are all cited references in this disclosure) that liposomes comprised of equal amounts of the cytofectin DOTMA (N-[1-(2,3-dioleyloxy)propyl]-N,N,N-trimethylammonium chloride) and neutral lipid DOPE (dioleoyl phosphotidylethanolamine) spontaneously associate with DNA to form efficient transfection complexes, the technology has advanced incrementally. There have been few cytofectins developed which have improved upon the in vivo activity of the prototypic agent DOTMA. This lack of progress may reflect funding priorities which have focused on the application of cationic lipid technology to biologic problems, rather than research focusing on principles which effect cytofectin-mediated gene delivery. Specifically, studies focused on the mechanism(s) involved in cytofectin actions, barriers to cytofectin-mediated in vivo gene delivery, and clarification of cytofectin structure/activity relationships would facilitate the development of improved cationic lipid-based delivery reagents. While research into the mechanism responsible for cationic amphiphile-mediated gene delivery is ongoing in a number of laboratories (Sternberg, B., Sorgi, F. L. and Huang, L. 1994. New structures in complex formation between DNA and cationic liposomes visualized by freeze-fracture electron microscopy. FEBS. Lett. 356(2–3): 361–6, Wrobel, I. and Collins, D. 1995. Fusion of cationic liposomes with mammalian cells occurs after endocytosis. Biochim. Biophys. Acta 1235(2): 296–304, and Zabner, J., Fasbender, A. J., Moninger, T., Poellinger, K. A. and Welsh, M. J. 1995. Cellular and molecular barriers to gene transfer by a cationic lipid. J. Biol. Chem. 270(32): 18997–9007), even the most basic aspects of the mechanism of action of cytofectins (the relative contributions of direct cytoplasmic membrane fusion and endocytosis) remain unresolved.

Currently, several cationic amphiphile preparations are commercially available, and new analogs have been published. However, these agents are frequently reported without comparison to existing compounds, and therefore it is difficult to derive insights into the relationship of structural motifs to polynucleotide transfection. This difficulty has been exacerbated by the variability in: 1) transfected cell types exploited in the initial report, 2) reporter genes used to characterize transfection, 3) methods for reporting biologic response (typically reporter protein expression) and 4) specific expression vector design. In addition, there have been few reports which describe the effects of alternative formulation methods. Paradoxically, the relative lack of such fundamental information implies that significant improvements in cytofectin-mediated gene transfer technology may be achieved by further systematic study.

As indicated above, various cationic lipids have been synthesized in previous references. In the realm of patents, for example, U.S. Pat. No. 4,812,449 discloses in situ active compound assembly of biologically active agents at target locations in preference to surroundings which are desired to be unaffected. Several charged and uncharged amine derivatives are described.

Introduced in U.S. Pat. No. 5,171,678 are lipopolyamines and their use for transfecting eukaryotic cells. A polynucleotide is mixed with the subject lipopolyamine and contacted with the cells to be treated.

U.S. Pat. Nos. 5,186,923 and 5,277,897 relate an enhancement of cellular accumulation of lipophilic cationic organometallic compounds by reduction of the intramembrane potential. Technetium containing compounds are disclosed.

Lipophilic cationic compounds are presented in U.S. Pat. No. 5,208,036. Asymmetrical amine compounds are synthesized and employed in a method for DNA transfection. The amines are quaternized by two hydrogens or alkyl, aryl, aralkyl, quinuclidino, piperidino, pyrrolidino, or morpholine groups, unlike the present invention.

U.S. Pat. No. 5,264,618 discloses cationic lipids for intracellular delivery of biologically active molecules. Asymmetric ammonium containing cationic lipids are presented for transporting molecules into membrane enclosed systems. The amines are quaternized by two hydrogens or alkyl groups, unlike the present invention.

Transfection of nucleic acids into animal cells via a neutral lipid and a cationic lipid is revealed in U.S. Pat. No. 5,279,833. Liposomes with nucleic acid transfection activity are formed from the neutral lipid and the ammonium salt containing cationic lipid.

U.S. Pat. No. 5,334,761 describes other amine containing cationic lipids. Cationic lipids are utilized to form aggregates for delivery of macromolecules and other compounds into cells. The amines are quaternized by two hydrogens or unbranched alkyl groups, unlike the present invention.

In the PCT publication of PCT/US94/13362 a heterocyclic diamine is disclosed. A symmetrical quaternary diamine having lipid tails is related for forming liposomes.

The foregoing patents and publication reflect the state of the art of which the applicants are aware and are tendered with the view toward discharging applicants' acknowledged duty of candor in disclosing information which may be pertinent in the examination of this application. It is respectfully submitted, however, that none of these patents teach or render obvious, singly or when considered in combination, applicants' claimed invention.

SUMMARY OF THE INVENTION

An object of the present invention is to disclose formulations, counterions, and conditions that yield lipid-:polynucleotide complexes formed from a category of amines that greatly facilitate the delivery of biologically active compounds through membrane structures.

Another object of the present invention is to present formulations, counterions, and conditions that yield lipid-:polynucleotide complexes formed from a group of cationic amine compounds that assist in the transport of selected macromolecules and other substances into and past membrane barriers.

A further object of the present invention is to relate formulations, counterions, and conditions that yield cytofectin:polynucleotide complexes formed from a collection of biologically active molecule transporters having the general structure:

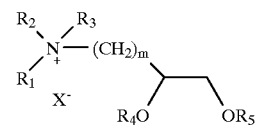

wherein m=1–10; $R_1$, $R_2$, and $R_3$ are the same or different and are hydrogen, an alkyl group, an alkenyl group, an alkynyl group, a hydroxylated alkyl, alkenyl, or alkynyl group, an ether containing alkyl, alkenyl, or alkynyl group, or a halogenated alkyl, alkenyl, or alkynyl group; $R_4$ is an alkyl group, an alkenyl group, an alkynyl group, or an alkyl, alkenyl, or alkynyl containing acyl group; $R_5$ is an alkyl group, an alkenyl group, an alkynyl group, or an alkyl, alkenyl, or alkynyl containing acyl group; and $X^-$ is an anion that assist in the transport of selected macromolecules and other substances into and past membrane barriers.

Yet another object of the present invention is to describe formulations, counterions, and conditions that yield cytofectin:polynucleotide complexes in which the transfection efficiency is influenced by the effective sizes of the complexes which in turn are a function of the application of sonicating energies and surrounding temperatures.

Still yet another object of the present invention is to disclose structural properties and counterions of cytofectins that influence transfection efficiency.

Disclosed are novel formulations, counterions, and heating/sonication conditions for producing transfection active cytofectin:polynucleotide complexes from cationic transporter molecules that facilitate the delivery of polynucleotides into and beyond membrane barriers or boundaries. Generally related is a cytofectin:polynucleotide complex that comprises a polynucleotide; a quaternized amine having bonded to an attached carbon chain at least a pair of same or different lipoyl moieties selected from a group consisting of an alkyl, alkenyl, alkynyl, alkanoyl, alkenoyl, or alkynoyl groups and at least two amine bonded hydroxylated, ether containing, or acyloxy containing alkyl, alkenyl, or alkynyl groups or at least one amine bonded halogen containing moiety selected from a group consisting of a halogenated alkyl, alkenyl, or alkynyl group or a mixture of at least one halogen containing moiety selected from a group consisting of a halogenated alkyl, alkenyl, or alkynyl group and at least one hydroxylated, ether containing, or acyloxy containing alkyl, alkenyl, or alkynyl group; and a counterion for the quaternized amine.

More specifically, compounds having the structure:

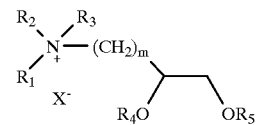

wherein m=1–10; $R_1$, $R_2$, and $R_3$ are the same or different and are hydrogen, an alkyl group, an alkenyl group, an alkynyl group, a hydroxylated alkyl, alkenyl, or alkynyl group, an ether containing alkyl, alkenyl, or alkynyl group, or a halogenated alkyl, alkenyl, or alkynyl group; $R_4$ is an alkyl group, an alkenyl group, an alkynyl group, or an alkyl, alkenyl, or alkynyl containing acyl group; $R_5$ is an alkyl group, an alkenyl group, an alkynyl group, or an alkyl, alkenyl, or alkynyl containing acyl group; and $X^-$ is a counterion. Usually, m is 1; $R_1$, $R_2$, and $R_3$ are alkyl groups and $R_4$ and $R_5$ are alkyl containing acyl groups and more commonly m=1; $R_1$ and $R_3$ are methyl or equivalent groups; $R_2$ is an ethyl or equivalent group; and $R_4$ and $R_5$ are $-CO(CH_2)_{12}CH_3$ or equivalent groups.

The subject cytofectin:polynucleotide complexes are produced by sonicating a mixture of the polynucleotide, the quarternized amine containing cytofectin, and the counterion for a selected period of time at a predetermined temperature. Usually, the selected period of time for sonication is about thirty seconds to about two minutes and the predetermined temperature is above a phase transition temperature of lipoyl moieties within the cytofectin and is about 40° C. to about 70° C., more usually about 50° C. to about 60° C., and preferably about 56° C.

Counterions that enhance transfection are bisulfate, trifluoromethanesulfonate, and the halides, in particular iodide and to a lesser extent bromide.

Preferred reaction conditions for generating transfection active cytofectin:polynucleotide complexes include elevated temperatures and the use of sonication during the formation of the complexes.

Other objects, advantages, and novel features of the present invention will become apparent from the detailed description that follows, when considered in conjunction with the associated drawings.

DESCRIPTION OF THE PREFERRED EMBODIMENT

Figure 1:
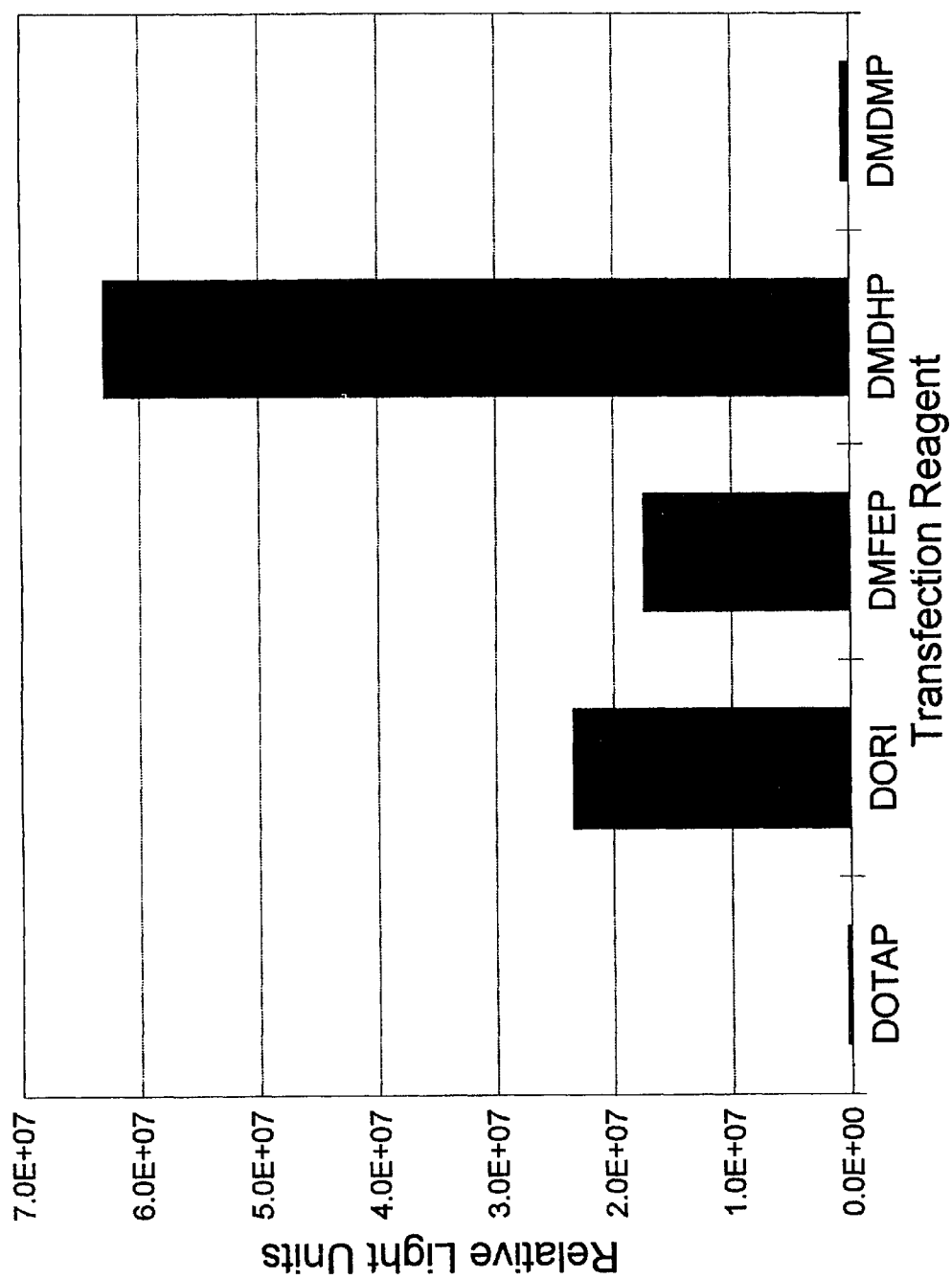
FIG. 1 shows a comparison of cytofectin-mediated DNA transfection using NIH 3T3 cells.

Cationic amphiphiles (cytofectins) are widely used for the transfection of cultured cells, and may become useful for the development of genetic medicines. Although fundamental research focused on clarification of physicochemical structure/biologic function correlations has been limited, general principles relating to optimization of cytofectin structure are beginning to emerge. The formulation studies disclosed here address the tendency of high concentration cytofectin:polynucleotide complexes to precipitate. From these observations, we show that what we believe to be thermodynamically stable products can be formed by sonication with heating of cytofectin:polynucleotide complexes, and that this process reduces the kinetically driven aggregation and precipitation which currently complicates many in vivo studies.

Referring now to the following disclosure and to the data presented in FIGS. 1–11, there are described preferred embodiments of formulations and conditions that yield cytofectin:polynucleotide complexes formed from a cationic monoamine having at least a pair of lipoyl moieties selected from a group consisting of an alkyl chain, an alkenyl chain, and an alkyl or alkenyl containing acyl chain such as:

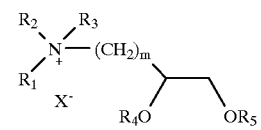

wherein m=1–10; $R_1$, $R_2$, and $R_3$ are the same or different and are hydrogen, an alkyl group, an alkenyl group, an alkynyl group, a hydroxylated alkyl, alkenyl, or alkynyl group, an ether containing alkyl, alkenyl, or alkynyl group, a halogenated alkyl, alkenyl, or alkynyl group, or acyl or acyloxy containing alkyl, alkenyl, or alkynyl group; $R_4$ is an alkyl group, an alkenyl group, an alkynyl group, or an alkyl, alkenyl, or alkynyl containing acyl group; $R_5$ is an alkyl group, an alkenyl group, an alkynyl group, or an alkyl, alkenyl, or alkynyl containing acyl group; and $X^-$ is an anion. The extra, with m more than 1, number of methylenes is introduced by standard procedures that complement the described subject synthetic pathways.

A first preferred structure is:

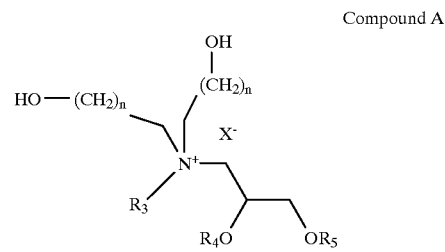

Compound A wherein for Compound A: n=1–10, usually between 1 and 3, preferably 1; $R_3$ is a hydrogen, an alkyl group, an alkenyl group, an alkynyl group, or a hydroxylated alkyl, alkenyl, alkynyl group, often an alkyl group of from 1 to 10 carbons, preferably a methyl group; $R_4$ and $R_5$ are the same or different with each an alkyl group, an alkenyl group, an alkynyl group, or an alkyl, alkenyl, or alkynyl containing acyl group; and $X^-$ is an anion, usually an oxyanion or halide counterion.

Generalized Synthesis Scheme For Compound A

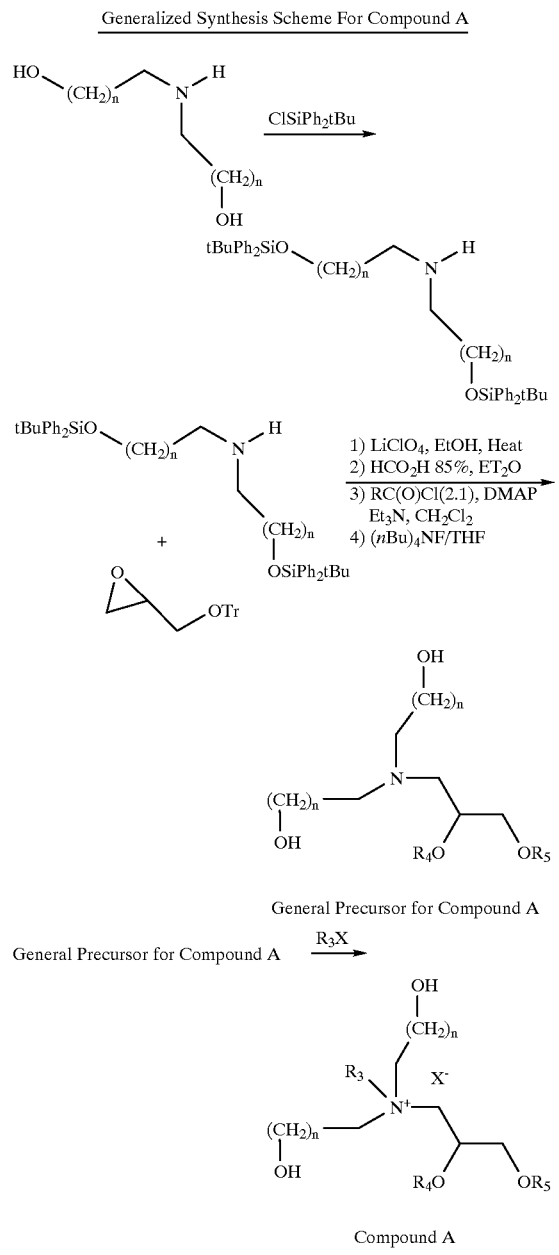

General Precursor for Compound A

Compound A where: the abbreviation Tr in the synthesis scheme denotes —C(Ph)$_3$, n=1–10, usually between 1 and 3, preferably 1; R$_3$ is a hydrogen, an alkyl group, an alkenyl group, an alkynyl group, or a hydroxylated alkyl, alkenyl, alkynyl group, often an alkyl group of from 1 to 10 carbons, preferably a methyl group; R$_4$ and R$_5$ are the same or different with each an alkyl group, an alkenyl group, an alkynyl group, or an alkyl, alkenyl, or alkynyl containing acyl group; and X$^-$ is an anion, usually an oxyanion or halide counterion. It is stressed that although other procedures are contemplated to be within the realm of this disclosure, a preferred method for introducing different acyl containing R$_4$ and R$_5$ groups in this compound, and in the compounds below, is the synthesis method given in "A Flexible Approach to Synthetic Lipid Ammonium Salts for Polynucleotide Transfection" by Bennett et al. (*Tetrahedron Letters*, Vol. 36, No. 13, pp. 2207–2210) and is herein incorporated by reference. In this method an acyl migration is employed to produce the mixed ester products.

In the general synthesis scheme for Compound A derivatives, the first step involves reacting a tert-butyldiphenylsilyloxy derivatized material (made via a reaction of the dihydroxyethyl starting material with ClSiPh$_2$tBu) with (triphenylmethoxy)methyloxirane (synthesized according to the procedure described in Bennett, M. J., Malone, R. W., and Nantz, M. H. *Tetrahedron Lett.* 1995, 36, 2207) in the presence of lithium perchlorate in absolute ethanol. Diethyl ether in formic acid comprised the second step. The third step is a reaction with an alkyl, alkenyl, or alkynyl halide or an alkyl, alkenyl, or alkynyl containing acyl halide. The fourth step is tetrabutylammonium fluoride and THF initiated removal of the tert-butyldiphenylsilyloxy protection groups to produce the general precursor compound. The general precursor compound is then allowed to react with a selected alkyl, alkenyl, alkynyl or hydroxylated alkyl, alkenyl, or alkynyl halide.

A second preferred structure is:

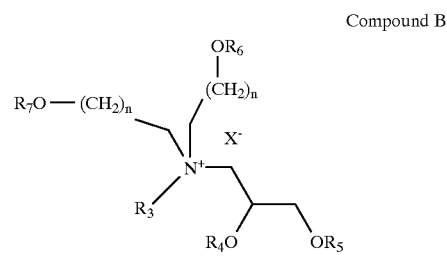

Compound B wherein for Compound B: n=1–10, usually between 1 and 3, preferably 1; R$_3$ is a hydrogen, an alkyl group, an alkenyl group, an alkynyl group, or a hydroxylated alkyl, alkenyl, alkynyl group, often an alkyl group of from 1 to 10 carbons, preferably a methyl group; R$_4$ and R$_5$ are the same or different with each an alkyl group, an alkenyl group, an alkynyl group, or an alkyl, alkenyl, or alkynyl containing acyl group; R$_6$ is an alkyl group, an alkenyl group, an alkynyl group, or an acyl containing group all from 1 to 10 carbons, preferably a methyl group; R$_7$ is an alkyl group, an alkenyl group, an alkynyl group, or an acyl containing group all from 1 to 10 carbons, preferably a methyl group; and X$^-$ is an anion, usually an oxyanion or halide counterion.

Generalized Synthesis Scheme For Compound B

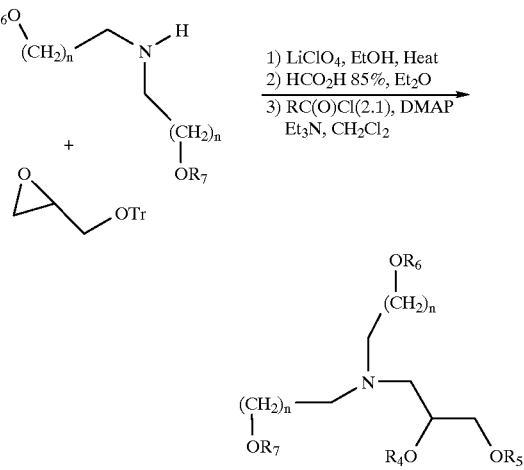

General Precursor for Compound B

-continued

General Precursor for Compound B $\xrightarrow{R_3X}$

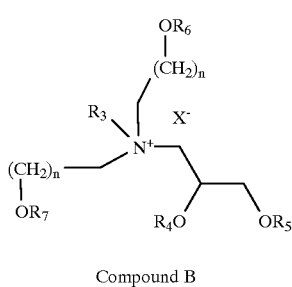

Compound B where: n=1–10, usually between 1 and 3, preferably 1; $R_3$ is a hydrogen, an alkyl group, an alkenyl group, an alkynyl group, or a hydroxylated alkyl, alkenyl, alkynyl group, often an alkyl group of from 1 to 10 carbons, preferably a methyl group; $R_4$ and $R_5$ are the same or different with each an alkyl group, an alkenyl group, an alkynyl group, or an alkyl, alkenyl, or alkynyl containing acyl group; $R_6$ is an alkyl group, an alkenyl group, an alkynyl group of from 1 to 10 carbons, preferably a methyl group; $R_7$ is an alkyl group, an alkenyl group, an alkynyl group of from 1 to 10 carbons, preferably a methyl group; and $X^-$ is an anion, usually an oxyanion or halide counterion.

In the general synthesis scheme for Compound B the first step involves reacting an amine starting material with (triphenylmethoxy)methyloxirane in the presence of lithium perchlorate in absolute ethanol. Diethyl ether in formic acid comprised the second step. The third step is a reaction with an alkyl alkenyl, or alkynyl halide or an alkyl, alkenyl, or alkynyl containing acyl halide. The general precursor compound is then allowed to react with a selected alkyl, alkenyl, alkynyl or hydroxylated alkyl, alkenyl, or alkynyl halide.

A third preferred structure is:

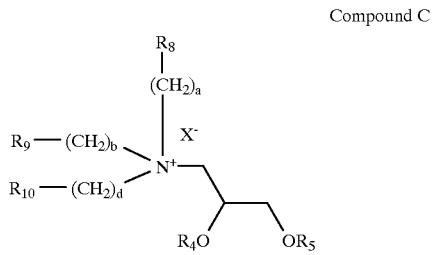

Compound C wherein for Compound C: a, b, or d are the same or different and are from 0–10, usually between 0 and 3, preferably 0 or 1; $R_4$ and $R_5$ are the same or different with each an alkyl group, an alkenyl group, an alkynyl group, or an alkyl, alkenyl, or alkynyl containing acyl group; $R_8$, $R_9$, or $R_{10}$ are the same or different with each an alkyl, alkenyl, or alkynyl group or halogenated alkyl, alkenyl, or alkynyl group as long as one is halogen containing; and $X^-$ is an anion, usually an oxyanion or halide counterion.

More specifically for Compound C a preferred structure is:

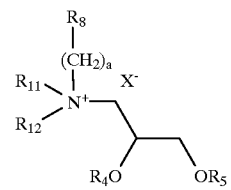

Compound C-1 wherein for Compound C: a=0–10, usually between 0 and 3, preferably 1; $R_4$ and $R_5$ are the same or different with each an alkyl group, an alkenyl group, an alkynyl group, or an alkyl, alkenyl, or alkynyl containing acyl group; $R_8$ is a halogenated alkyl, alkenyl, or alkynyl group, preferably a trifluoromethyl group; $R_{11}$ and $R_{12}$ are the same or different with each an alkyl, alkenyl, or alkynyl group or halogenated alkyl, alkenyl, or alkynyl group; and $X^-$ is an anion, usually an oxyanion or halide counterion.

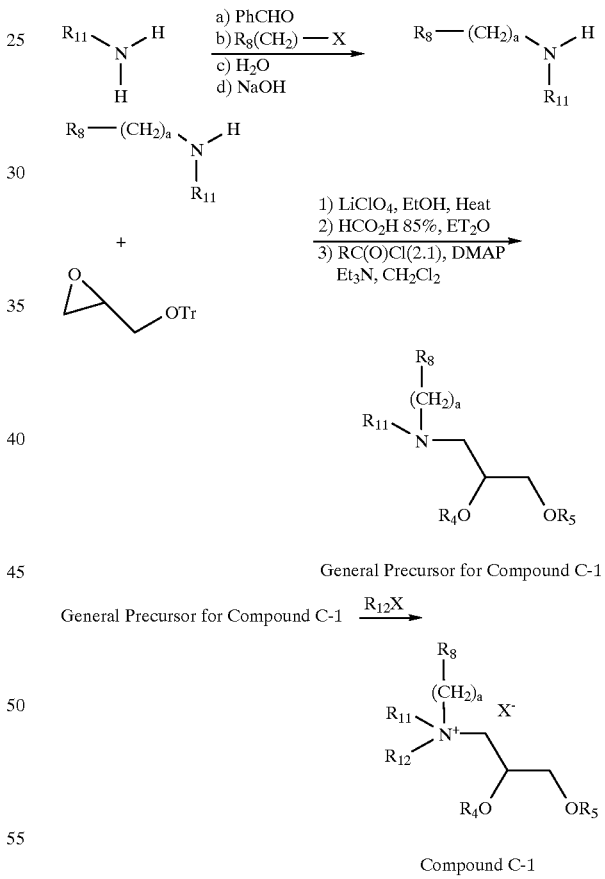

where: a=0–10, usually between 0 and 3, preferably 1; $R_4$ and $R_5$ are the same or different with each an alkyl group, an alkenyl group, an alkynyl group, or an alkyl, alkenyl, or alkynyl containing acyl group; $R_8$ is an alkyl, alkenyl, or alkynyl group or halogenated alkyl, alkenyl, or alkynyl group, preferably a trifluoromethyl group; $R_{11}$ and $R_{12}$ are the same or different with each an alkyl, alkenyl, or alkynyl group or halogenated alkyl, alkenyl, or alkynyl group; and $X^-$ is an anion, usually an oxyanion or halide counterion.

In the general synthesis scheme for Compound C-1 the first step involves reacting the preferably halogenated starting material with (triphenylmethoxy)methyloxirane in the presence of lithium perchlorate in absolute ethanol. A reaction with diethylether in formic acid comprised the second step. The third step is a reaction with an alkyl alkenyl, or alkynyl halide or an alkyl, alkenyl, or alkynyl containing acyl halide. The general precursor compound is then allowed to react with a selected alkyl, alkenyl, alkynyl or hydroxylated alkyl, alkenyl, alkynyl, halogenated $R_{11}$ and $R_{12}$ that are the same or different with each an alkyl, alkenyl, or alkynyl group or halogenated alkyl, alkenyl, or alkynyl group halide.

With even more specificity, three preferred structures will now be presented with specific synthesis schemes (detailed in the Example section below).

A first specific preferred structure is:

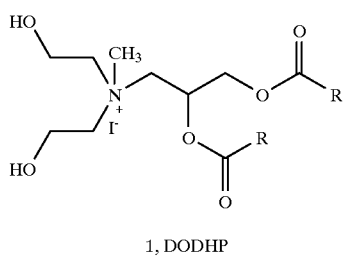

1, DODHP

Specific Synthesis Scheme for DODHP

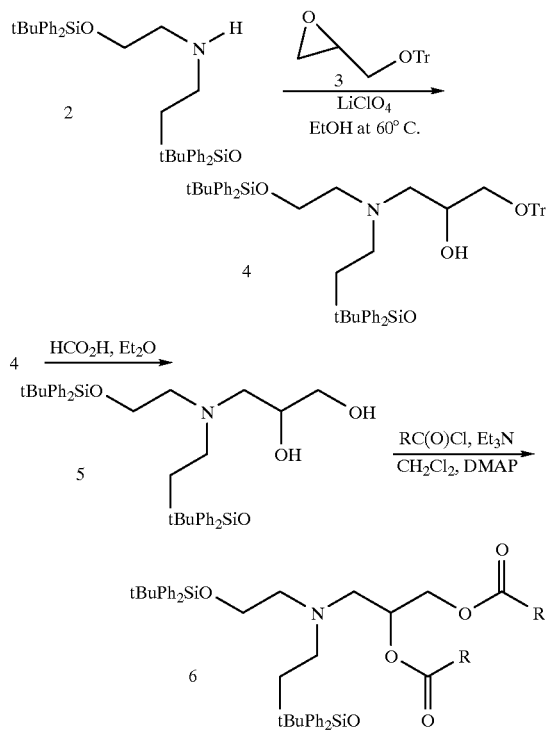

(where R = ——$CH_2(CH_2)_6CH=CH(CH_2)_7CH_3$)

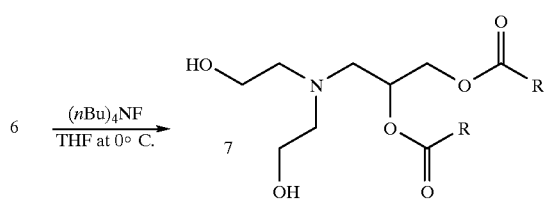

(where R = ——$CH_2(CH_2)_6CH=CH(CH_2)_7CH_3$)

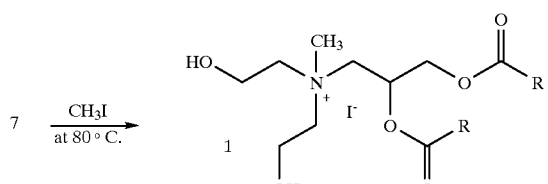

(where R = ——$CH_2(CH_2)_6CH=CH(CH_2)_7CH_3$)

A second specific preferred structure is:

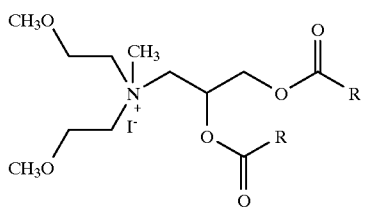

8, DODMP

Specific Synthesis Scheme for DODMP

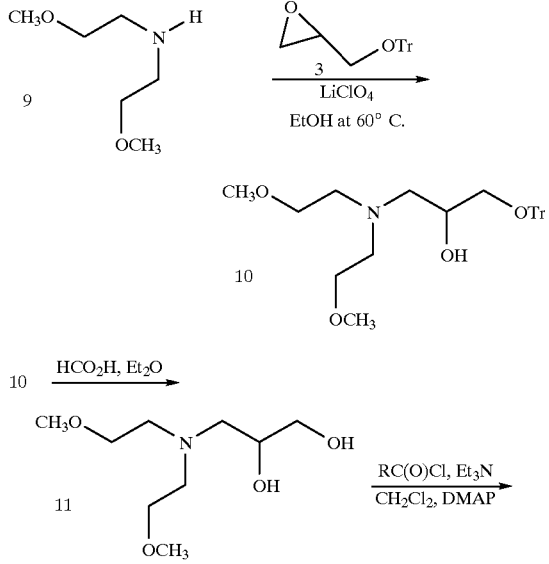

13

-continued

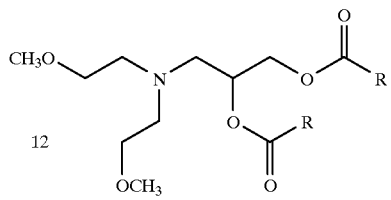

(where R = —CH$_2$(CH$_2$)$_6$CH=CH(CH$_2$)$_7$CH$_3$)

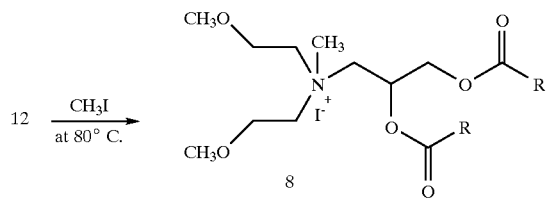

(where R = —CH$_2$(CH$_2$)$_6$CH=CH(CH$_2$)$_7$CH$_3$)

A third specific preferred structure is:

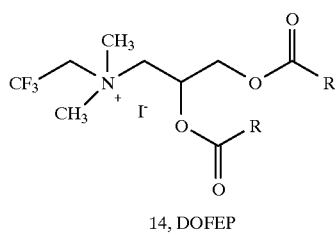

14, DOFEP

There are alternate synthesis pathways for the fluorinated derivatives, two of which are presented below, but other pathways, as with the above synthesis schemes, are considered within the realm of this disclosure.

A First Specific Synthesis Scheme for DOFEP

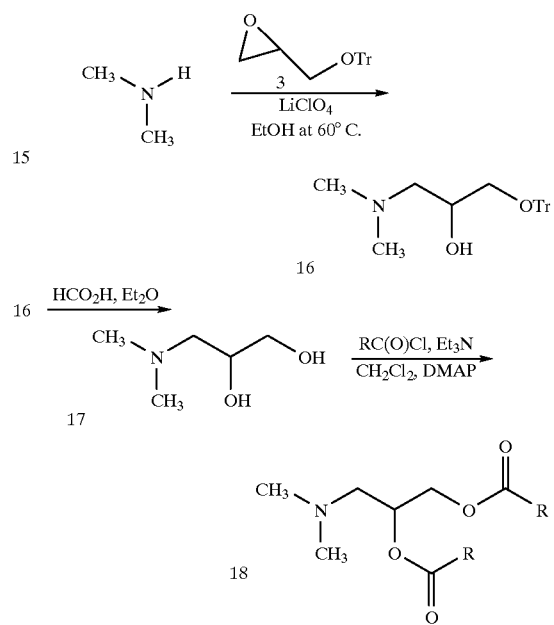

(where R = —CH$_2$(CH$_2$)$_6$CH=CH(CH$_2$)$_7$CH$_3$)

14

-continued

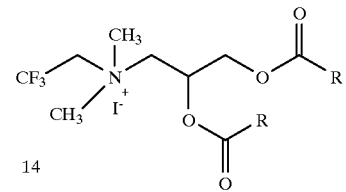

(where R = —CH$_2$(CH$_2$)$_6$CH=CH(CH$_2$)$_7$CH$_3$)

Compound 17, immediately above, may purchased directly from Aldrich Chemical Company and is usually ordered from this source.

A Second Specific Synthesis Scheme for DOFEP

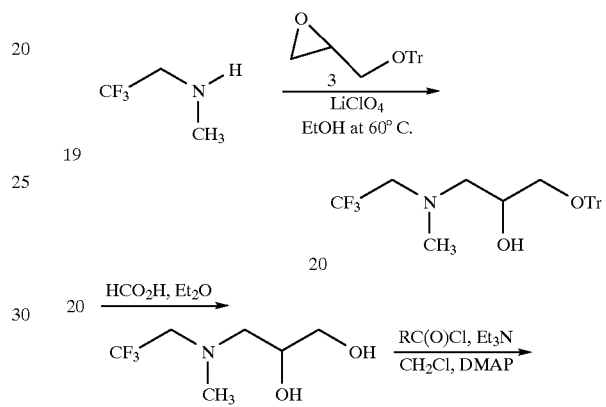

(where R = —CH$_2$(CH$_2$)$_6$CH=CH(CH$_2$)$_7$CH$_3$)

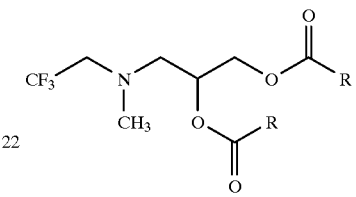

(where R = —CH$_2$(CH$_2$)$_6$CH=CH(CH$_2$)$_7$CH$_3$)

Note that Compound 19 was prepared from 2,2,2-trifluoroethylamine (Aldrich Chemical Company) according to a literature procedure by Wawzonek, S., McKillip, W., and Peterson, C. J. *Organic Synthesis, Coll.* Vol. V 1973, 758.

General Implications for Synthetic Flexibility

The subject synthesis schemes present opportunities for a widely flexible array of approaches to synthesizing related amine cationic transport molecules. Not only are monosubstituted amine transporters easily synthesized by the subject procedures, but so a disubstituted and trisubstituted derivatives with like or mixed polar domain functional groups readily produced. Either a monosubstituted or disubstituted amine starting material is utilized to generate one or two functional groups in the final compound or during the quaternization step a functional group containing residue is added (see the fluoronated example above).

By way of example and not by way of limitation, a mixed product is synthesized as follows:

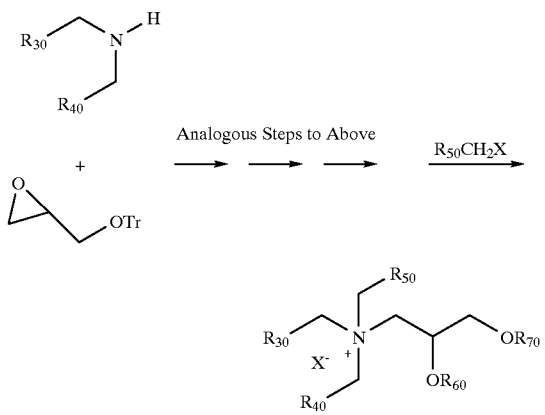

wherein $R_{30}$, $R_{40}$, and $R_{50}$ are the same or different and are a hydrogen, alkyl, alkenyl, or alkynyl group, a hydroxy or ether containing alkyl, alkenyl, or alkynyl group, or a halogen containing alkyl, alkenyl, or alkynyl group, $R_{60}$ and $R_{70}$ are carbonyl containing or not containing alkyl, alkenyl, or alkynyl groups, and $X^-$ is an oxyanion or halide counterion (note that the initial starting material functional group or groups may need to be protected via silation or other appropriate means). More specifically, a preferred synthesis scheme for a mixed functional product is:

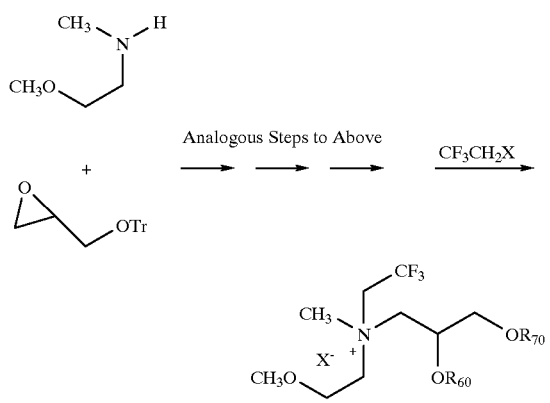

wherein $R_{60}$ and $R_{70}$ are carbonyl containing or not containing alkyl, alkenyl, or alkynyl groups and $X^-$ is an oxyanion or halide counterion.

An example of a synthesis that produces a trisubstituted derivative is as follows:

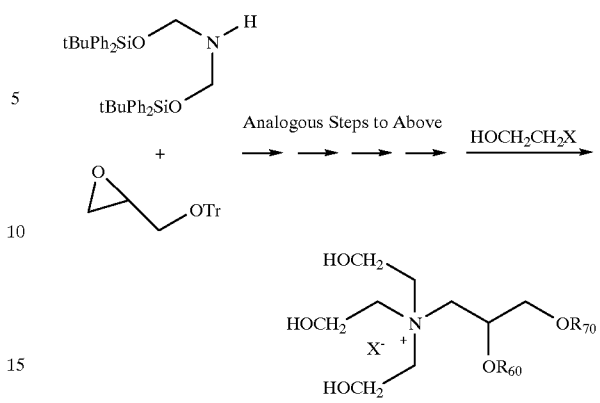

Cytofectin Structural Domains

Cytofectins can be defined by three principal structural motifs (FIG. 4): a cationic polynucleotide binding domain (I), a negatively charged counterion (II), and a hydrophobic domain (III). The chemical nature of these domains dictates the biophysical properties exhibited by the cytofectins. Thus, structural modifications within each motif can result in significant alterations in the behavior of pharmaceuticals containing these amphiphiles. For this reason, researchers have attempted to correlate biophysical properties, compound structure, and functional assessments of polynucleotide transfection.

Polar Domain Structural Considerations

In general, various functionalities have been incorporated into cytofectin polar domains. Many of these functionalities are known to modulate the binding and condensation of polynucleotides into cytofectin:polynucleotide complexes. These polynucleotide binding domains, usually comprised of nitrogen-based groups, are cationic either as a consequence of their basicity in aqueous solutions, or via N-alkylation to yield quaternary amines. Researchers have prepared several cytofectins which contain a variety of nitrogen-based functionality including: tetraalkylammonium (Felgner, P. L., Gadek, T. R., Holm, M., Roman, R., Chan, H. W., Wenz, M., Northrop, J. P., Ringold, G. M. and Danielsen, M. 1987. Lipofection: a highly efficient, lipid-mediated DNA-transfection procedure. Proc. Natl. Acad. Sci. U.S.A. 84(21): 7413–7, Leventis, R. and Silvius, J. R. 1990. Interactions of mammalian cells with lipid dispersions containing novel metabolizable cationic amphiphiles. Biochim. Biophys. Acta 1023(1): 124–32, and Felgner, J. N., Kummar, R., Sridhar, C. N., Wheeler, C., Tsai, Y. J., Border, R., Ramsay, P., Martin, M. and Felgner, P. 1994. Enhanced gene delivery and mechanism studies with a novel series of cationic lipid formulations), polyammonium (Behr, J. P., Demeneix, B., Loeffler, J. P. and Perez-Mutul, J. 1989. Efficient gene transfer into mammalian primary endocrine cells with lipopolyamine-coated DNA. Proc. Nati. Acad. Sci. U.S.A. 86(18): 6982–6, Zhou, X. H., Klibanov, A. L. and Huang, L. 1991. Lipophilic polylysines mediate efficient DNA transfection in mammalian cells. Biochim. Biophys. Acta 1065(1): 8–14, and Puyal, C., Milhaud, P., Bienvenue, A. and Philippot, J. R. 1995. A new cationic liposome encapsulating genetic material. A potential delivery system for polynucleotides. Eur. J. Biochem. 228(3): 697–703), monoalkylammonium (Gao, X. A. and Huang, L. 1991. A novel cationic liposome reagent for efficient transfection of mammalian cells. Biochem. Biophys. Res. Commun. 179 (1): 280–5), and amidine-based (Ruysschaert, J. M., el Ouahabi, A., Willeaume, V., Huez, G., Fuks, R., Vandenbranden, M. and Di Stefano, P. 1994. A novel cationic amphiphile for transfection of mammalian cells. Biochem. Biophys. Res. Commun. 203(3): 1622–8). Such functionality may have an influence on the efficiency with which polynucleotides interact with cationic lipid particles, the interactions between lipid/DNA complexes and biological membranes, and the mechanism(s) by which these complexes deliver polynucleotides into the cells. Therefore, studies correlating polar domain chemical structure and physical properties with transfection activity would be predicted to clarify the role of polar domain hydration and intermolecular bonding on polynucleotide delivery. Such a study is presented herein.

A number of investigations into polar domain structure/activity relationships have been reported. Previous studies have focused on the optimization of the alkyl chain length separating the lipidic domain and polynucleotide binding group (Ito, A., Miyazoe, R., Mitoma, J., Akao, T., Osaki, T. and Kunitake, T. 1990. Synthetic cationic amphiphiles for liposome-mediated DNA transfection. Biochem. Int. 22(2): 235–41 and Farhood, H., Bottega, R., Epand, R. M. and Huang, L. 1992. Effect of cationic cholesterol derivatives on gene transfer and protein kinase C activity. Biochim. Biophys. Acta 1111(2): 239–46); correlations between cationic functionality (tetraalkylammonium vs. trialkylammonium), protein kinase C activity, and transfection efficacy (Farhood, H., Bottega, R., Epand, R. M. and Huang, L. 1992. Effect of cationic cholesterol derivatives on gene transfer and protein kinase C activity. Biochim. Biophys. Acta 1111(2): 239–46); and correlations between headgroup charge density and transfection activity (Remy, J. S., Sirlin, C., Vierling, P. and Behr, J. P. 1994. Gene transfer with a series of lipophilic DNA-binding molecules. Bioconjug. Chem. 5(6): 647–54). Subsequently, the subject research was conducted to explore the correlations between transfection activity and functional modifications of the tetraalkylammonium moiety used to bind anionic regions of DNA, RNA, and related polymers. The decision to use tetraalkylammonium-derivatized cytofectins for this study was based on unpublished observations that tertiary ammonium analogs of DOTMA-related compounds are not active transfection agents.

Evidence supporting the hypothesis that modifications in cytofectin headgroup structure (and associated physical properties) can influence transfection activity comes from research performed by Feigner et al. (Felgner, J. N., Kummar, R., Sridhar, C. N., Wheeler, C., Tsai, Y. J., Border, R., Ramsay, P., Martin, M. and Felgner, P. 1994. Enhanced gene delivery and mechanism studies with a novel series of cationic lipid formulations. J. Biol. Chem. 269(4): 2550–2561) and our laboratories (Bennett, M. J., Malone, R. W. and Nantz, M. H. 1995. A flexible approach to synthetic lipid ammonium salts for polynucleotide transfection. Tetrahedron Lett. 36(1): 2207–2210 and Balasubramaniam, R. P., Bennett, M. J., Aberle, A. M., Malone, J. G., Nantz, M. H. and Malone, R. W. 1996. Structural and functional analysis of cationic transfection lipids: the hydrophobic domain. Gene Ther. 3(2): 163–172). These studies have shown that cytofectins which incorporate a hydroxyethyl-derivatized tetraalkylammonium group in their polar domain demonstrate enhanced transfection activity when compared to analogs which do not incorporate such groups (e.g., DORI vs. DOTAP).

We postulate that variations in the chemical composition of the tetraalkylammonium group of cytofectins might effect transfection activity by: 1) influencing cationic liposome/polynucleotide interactions during formulation, 2) altering interactions between cationic liposome/polynucleotide complexes and cell membranes, 3) altering pathways by which these complexes enter cells, 4) altering intracellular trafficking of lipid:polynucleotide complexes, and 5) altering the disassociation of the lipid:polynucleotide complex. We hypothesize that the covalent attachment of select functional groups, like the hydroxyethyl group, to the ammonium moiety can influence both lipid surface hydration and the effective charge of the ammonium group. These effects can alter the cytofectins' transfection activity by influencing one or more of the above processes.

Surface hydration may be one important property by which modifying the polar domain may alter cytofectin transfection activity. The degree of lipid surface hydration can influence intermolecular lipid interactions both prior to and following addition of polynucleotide. Such effects might occur via a variety of interactions. The addition of alkyl groups of increasing chain length to the ammonium group could weaken intermolecular lipid interactions by increasing the cross-sectional area of the headgroup (steric effects). The presence or absence of functional groups which can participate in hydrogen bond formation as either acceptors or donors will effect hydration, interaction with polynucleotide, and bonding to adjacent lipids (e.g. cytofectins, DOPE or cellular lipids). The inclusion of electron withdrawing functionality may influence the effective cationic charge of the binding domain through an inductive effect. However, these complex interactions make it difficult to identify the principal factors influencing cytofectin transfection activity. An example is the inclusion of functional groups capable of hydrogen bonding. In this example, either stronger or weaker lipid-lipid interactions might arise as a consequence of 1) intermolecular hydrogen bonding or 2) increased headgroup hydration respectively. Thus, we chose to empirically analyze the effect of such alterations on the DNA transfection activity.

In order to test hypotheses pertaining to lipid surface hydration and effective cationic charge, a panel of cationic amphiphiles (see FIG. 5) were prepared by simple N-alkylation of N,N-dimethyl-1,2-dimyristoyloxy-3-aminopropane with the corresponding alkyl halide, using a procedure analogous to that used by Felgner et al. (Felgner, J. N., Kummar, R., Sridhar, C. N., Wheeler, C., Tsai, Y. J., Border, R., Ramsay, P., Martin, M. and Felgner, P. 1994. Enhanced gene delivery and mechanism studies with a novel series of cationic lipid formulations. J. Biol. Chem. 269(4): 2550–2561). Lipid thin-films containing these amphiphiles and an equal molar amount of DOPE were hydrated using sterile deionized water, mixed with the plasmid DNA pNDCLUX (Aberle, A. M., Bennett, M. J., Malone, R. W. and Nantz, M. H. 1996. The counterion influence of cationic lipid-mediated transfection of plasmid DNA. Biochim. Biophys. Acta 1299(3): 281–283), (encoding the $P.$ $pyralis$ luciferase) and the resulting complexes were used to transfect NIH 3T3 murine fibroblast cells. The experimental design is outlined in FIG. 5. Based on the transfection data obtained from this experiment (see FIG. 6), the following conclusions can be made: 1) Of the lipids selected to examine correlations between lipid polar domain cross sectional area and transfection activity, DMEAP (see Example 19 below and FIG. 5 for the exact structure of this cytofectin and the cytofectins referred to below) had the highest levels of plasmid transfection activity. 2) Of the lipids selected to test the influences of hydrogen bonding, both the methyl ether containing lipid DMMEP and the hydroxyethyl containing lipid showed a 2-fold enhancement over DMPAP, which has no hydrogen bonding capabilities. We observed no correlation between the number or modes of hydrogen bonding (acceptor vs. donor). Polar domain influences on the transfection ability of selected compounds are presented below (see FIGS. 6, in vitro, and 7, in vivo).

Counterion Considerations

All positively charged cytofectin polar domains incorporating monoalkylammonium, polyammonium, or tetraalkylammonium-based functionality, have an associated negatively charged counterion. Monoalkylammonium and polyammonium-containing lipids typically have one or more hydroxide counterions as a consequence of ammonium salt formation resulting from the basicity of the corresponding primary, secondary, or tertiary amine in aqueous media. Tetraalkylammonium-based cytofectins acquire their negatively charged counterion when the ammonium salt is formed as a result of N-alkylation.

As a result of the association of the negatively charged counterion with the positively charged polynucleotide binding domain, we believe that the chemical nature of the counterion may effect the physicochemical properties of cytofectins. Specifically, the counterion could influence lipid surface hydration, vesicle fluidity, and lipid polymorphism. Therefore, the counterion could also influence the transfection activity of cytofectins.

In order to study possible counterion influences on cytofectinmediated transfection activity, a panel of DOTAP (N-[1,2,3-dioleoyloxy)propyl]-N,N,N-trimethylammonium) analogs, differing only in the anionic counterion, were prepared using ion exchange chromatography (Aberle, A. M., Bennett, M. J., Malone, R. W. and Nantz, M. H. 1996. The counterion influence of cationic lipid-mediated transfection of plasmid DNA. Biochim. Biophys. Acta 1299(3): 281–283). The series of counterions (Table 1) were selected so that direct comparisons between anion-water interactions could be made. Previous studies have shown that there is a correlation between membrane behavior in various salt solutions and the nature of the anions categorized according to the Hofmeister series (Epand, R. M. and Bryszewska, M. 1988. Modulation of the bilayer to hexagonal phase transition and solvation of phosphatidylethanolamines in aqueous salt solutions. Biochemistry 27(24): 8776–9, Koynova, R. D., Tenchov, B. G. and Quinn, P. J. 1989. Sugars favour formation of hexagonal (HII) phase at the expense of lamellar liquid-crystalline phase in hydrated phosphatidylethanolamines. Biochim. Biophys. Acta 980: 377–380, and Collins, K. D. and Washabaugh, M. W. 1985. The Hofmeister effect and the behaviour of water at interfaces. Q. Rev. Biophys. 18(4): 323–422), which groups ions as either kosmotropes (water structuring) or chaotropes (water destabilizing) (see Table 1).

TABLE 1

Summary of cytofectin counterions

| Kosmotropes | Chaotropes |
|---|---|
| $HSO_4^{-1}$ | $I^-$ |
| $CF_3SO_3^{-1}$ | $Br^-$ |
| $H_2PO_4$ | $Cl^-$ |
| $SO_4^{-2}$ | $CH_3C(O)O^-$ |

Transfection analyses using these cytofectins were performed in vitro (NIH 3T3 murine fibroblasts), and in vivo (intratracheal instillation into mice) with excellent correlation between the in vitro (FIG. 8) and in vivo (FIG. 9) data. One may infer that the trends observed in these screenings may be applicable to a variety of cell types. Furthermore, the data suggests that the highly delocalized polar kosmotropic oxyanions, bisulfate and trifluoromethanesulfonate (triflate), promote the highest levels of luciferase expression. Among the halogens examined, the DOTAP iodide analog was the most active. It is believed that iodide most closely associates with the alkylammonium headgroup due to electrostatic interactions, while oxyanions competitively bind water away from the lipid surface. Thermodynamic arguments have suggested that lipid:solvent interactions directly influence lipid polymorphism. Thus, there may be an exclusion of water and closer interchain packing. In conclusion, these results indicate that incorporation of anions which can facilitate dehydration of the cytofectin polar domain leads to increased cytofectin transfection activity.

Hydrophobic Domain Structural Considerations

There are two types of hydrophobic domains which have been used in the design of cytofectins; sterol-based and di-acyl/alkyl-based domains. The hydrophobic domain, which can serve as a scaffold from which a lipid bilayer structure is built, also modulates bilayer fluidity and lipid polymorphism. Increased bilayer fluidity can lead to more efficient formation of lipid:DNA complexes and enhanced fusion of cytofectin:DNA complexes with cell or endosomal membranes, which is likely to be a key mechanistic step of the transfection process. While the contribution of sterol hydrophobic domains to bilayer fluidity is primarily dependent on the relative concentration of the sterol in the lipid particle, it is the chemical structure of the aliphatic groups contained in di-acyl/alkyl-based lipids which dictate their contribution to membrane fluidity.

It has been previously stated that there is a direct correlation between cytofectin transfection activity and transfection lipid bilayer fluidity. This hypothesis was originally forwarded by Akao et al. (Akao, T., Osaki, T., Mitoma, J., Ito, A. and Kunitake, T. 1991. Correlation between Physicochemical Characteristics of Synthetic Cationic Amphiphiles and Their DNA Transfection Ability. Bull. Chem. Soc. Jpn. 64: 3677), and suggests that one primary requirement of an amphiphile for DNA transfection is that the $T_c$ (phase transition temperature between the gel and liquid crystalline phases) be lower than 37° C., so that the transfection lipid assumes a fluid liquid crystalline state at cell culture temperatures. Research supporting this hypothesis (Felgner, J. N., Kummar, R., Sridhar, C. N., Wheeler, C., Tsai, Y. J., Border, R., Ramsay, P., Martin, M. and Felgner, P. 1994. Enhanced gene delivery and mechanism studies with a novel series of cationic lipid formulations. J. Biol. Chem. 269(4): 2550–2561 and Akao, T., Osaki, T., Mitoma, J., Ito, A. and Kunitake, T. 1991. Correlation between Physicochemical Characteristics of Synthetic Cationic Amphiphiles and Their DNA Transfection Ability. Bull. Chem. Soc. Jpn. 64: 3677) has relied on analysis of a limited number of cytofectin analogs and cell lines. In interpreting such studies, we believe it is important that results be obtained using multiple cell lines or tissues before drawing general conclusions correlating hydrophobic domain structure, bilayer physical properties, and transfection activity (Balasubramaniam, R. P., Bennett, M. J., Aberle, A. M., Malone, J. G., Nantz, M. H. and Malone, R. W. 1996. Structural and functional analysis of cationic transfection lipids: the hydrophobic domain. Gene Ther. 3(2): 163–172). It should be noted that, as of now, there is no evidence that the fluidity of neat cytofectin lipids predicts the fluidity of lipidic structures when bound to polynucleotide.

The bilayer fluidity of liposomes containing di-acyl/alkyl-based cytofectins can be modified by manipulating the symmetry (see Table 2), chain length, and saturation of the aliphatic groups contained in these lipids. In order to understand the relationships between cytofectin hydrophobic domain structure and transfection activity, we prepared a panel of cytofectins differing only in the composition of the aliphatic groups contained in the hydrophobic domain (Balasubramaniam, R. P., Bennett, M. J., Aberle, A. M., Malone, J. G., Nantz, M. H. and Malone, R. W. 1996. Structural and functional analysis of cationic transfection lipids: the hydrophobic domain. Gene Ther. 3(2): 163–172). Cytofectins examined in this study included compounds with both symmetric and dissymmetric hydrocarbon side chains which varied in length from C18:1 to C8:0. A previous report (Felgner, J. N., Kummar, R., Sridhar, C. N., Wheeler, C., Tsai, Y. J., Border, R., Ramsay, P., Martin, M. and Feigner, P. 1994. Enhanced gene delivery and mechanism studies with a novel series of cationic lipid formulations. J. Biol. Chem. 269(4): 2550–2561) also examined a similar series of cytofectins. However, only symmetric hydrocarbon side chains varying in length form C18:1 to C14:0 were examined using a single cell line (COS-7). This previous study indicated that the dimyristyl-containing compound DMRIE was most effective for DNA transfection of COS-7 cells. Since shorter side chains were not examined, the minimal effective acyl chain length was not defined. Cationic liposomes containing these cytofectins were formulated using 1:1 molar ratios of the cytofectin and DOPE. Transfection studies using NIH 3T3 murine fibroblast cells (see FIG. 10), CHO cells, and a cultured respiratory epithelial cell line (16HBE14o-) (see FIG. 11) revealed some intriguing observations. These are: 1) no single symmetric or dissymetric analog was most effective for DNA transfection of either cell line examined, 2) dissymmetric lipids resulted in levels of luciferase expression that were equal to or better than the most active symmetric lipid analogs, 3) dissymmetric cytofectins with shorter side chains (C12:0, C14:0) were among the most active lipids in the cell lines screened, and 4) the dioctanoyl (di C8:0) compound was generally the least active, indicating that the effective lower limit of fatty acyl chain length is defined at C(12).

TABLE 2

Summary of symmetric and dissymmetric cytofectins.

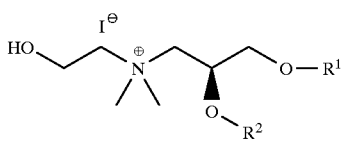

| Cytofectin | R$^1$ | R$^2$ |
|---|---|---|
| DORI | Oleoyl (18:1) | Oleoyl (18:1) |
| DPRI | Palmitoyl (16:0) | Palmitoyl (16:0) |
| DMRI | Myristoyl (14:0) | Myristoyl (14:0) |
| DLRI | Lauroyl (12:0) | Lauroyl (12:0) |
| DO'RI | Octanoyl (8:0) | Octanoyl (8:0) |
| OPRI | Oleoyl (18:1) | Palmitoyl (16:0) |
| PORI | Palmitoyl (16:0) | Oleoyl (18:1) |
| OO'RI | Oleoyl (18:1) | Octanoyl (8:0) |
| O'ORI | Octanoyl (8:0) | Oleoyl (18:1) |
| MLRI | Myristoyl (14:0) | Lauroyl (12:0) |
| LMRI | Lauroyl (12:0) | Myristoyl (14:0) |

Formulation Considerations

Cytofectins spontaneously form transfection complexes with a variety of biological polymers upon mixing in aqueous solvent. The mixing or formulation protocols used to prepare active transfection complexes currently involve optimization of; 1) the ratio of cationic lipid:neutral lipid, 2) solvent type, and 3) the molar ratio of cationic charge:polynucleotide phosphate charge.

Many optimized formulations incorporate Dioleoylphosphatidyl-ethanol-amine (DOPE) along with the cytofectin prior to mixing with DNA, although the high activity frequently observed with neat DOTAP indicates that DOPE is not always required. DOPE is known to be a strong destabilizer of lipid bilayers (Litzinger, D and Huang, L. 1992. Phosphatidylethanolamine liposomes: drug delivery, gene transfer and immunodiagnostic applications. Biochim. Biophys. Acta 1113, 201–227), and hence can enhance the intrinsic fusogenic properties of many cytofectins. Empirical optimization of cytofectin:DOPE molar ratio for various cell lines, tissues, and cytofectins can result in marked enhancement of transfection activity for the chosen application. In our hands, the optimized molar ratio has ranged from 9:1 to 1:2 (cytofectin:DOPE).

Cell culture experiments typically employ a formulation solvent consisting of either the media in which the cell line is cultured, or OptiMem (Gibco/BRL), a serum-free media which is enriched in factors including transferrin and various growth factors. The enhanced transfection activity which can be observed with OptiMem may reflect incorporation of the added biologically active agents into the lipid:polynucleotide complex. In such cases, binding to cell surface may be facilitated by specific ligand:receptor interactions. Complexes are typically prepared for in vivo administration using either water for injection or isotonic solvents such as physiologic saline. In contrast to cell culture results, solvent-specific enhancement has not been reported.

Molar cytofectin:polynucleotide phosphate charge ratio employed during formulation is frequently not reported, but typically ranges from 1:1 to 4:1 for cultured cells. Protocols for in vivo application, and particularly for pulmonary transfection, frequently employ strikingly different molar charge ratios. Yoshimura (Yoshimura, K., Rosenfeld, M. A., Nakamura, H., Scherer, E. M., Pavirani, A., Lecocq, J. P. and Crystal, R. G. 1992. Expression of the human cystic fibrosis transmembrane conductance regulator gene in the mouse lung after in vivo intratracheal plasmid-mediated gene transfer. Nucleic Acids Res. 20(12): 3233–40) first described the use of very low cytofectin:DNA charge ratios for pulmonary delivery, and performed an in vivo charge titration ranging from approximately 1:2.5 to 1:35. Optimal activity was obtained using the 1:35 ratio of cytofectin:DNA charge. This in vivo protocol also employed up to 1.4 milligram of plasmid/200 microliter injection, a 1,000 to 10,000 fold higher concentration of polynucleotide than is typically used for transfection of cultured cells. As the direct injection of free plasmid DNA into murine lung can result in significant levels of reporter gene expression (Yoshimura, K., Rosenfeld, M. A., Nakamura, H., Scherer, E. M., Pavirani, A., Lecocq, J. P. and Crystal, R. G. 1992. Expression of the human cystic fibrosis transmembrane conductance regulator gene in the mouse lung after in vivo intratracheal plasmid-mediated gene transfer. Nucleic Acids Res. 20(12): 3233–40, Meyer, K. B., Thompson, M. M., Levy, M. Y., Barron, L. G. and Szoka, F. C. 1995. Intratracheal gene delivery to the mouse airway: characterization of plasmid DNA expression and pharmacokinetics Gene Ther. 2(7):

450–60, and Balasubramaniam, R. P., Bennett, M. J., Aberle, A. M., Malone, J. G., Nantz, M. H. and Malone, R. W. 1996. Structural and functional analysis of cationic transfection lipids: the hydrophobic domain. Gene Ther. 3(2): 163–172), it is conceivable that complexes formulated with very low cytofectin:DNA ratios are not the active principle in the observed pulmonary transfections. We hypothesize that the transfection activity observed by Yoshimura et al. reflects the activity of unbound or minimally bound polynucleotide. In this case, the enhanced transfection activity which was observed upon adding small quantities of lipofectin to concentrated plasmid DNA may reflect partial protection from nucleases, rather than lipid-mediated transfection which occurs in cell culture. We have observed that similar charge titration experiments employing 20 micrograms of plasmid DNA/200 microliters result in optimized cytofectin:DNA charge ratios of 2:1 to 3:1, depending on cytofectin type and DOPE ratio.

High concentration lipid:DNA complexes (2:1 lipid:DNA charge ratio, 0.1 mg/ml or greater) are relatively insoluble, and tend to precipitate during formulation (see Table 3). We have observed that such precipitates are relatively inactive as transfection agents both in cell culture and in vivo. Furthermore, even apparently stable lipid:polynucleotide emulsions can precipitate when stored at room temperature for prolonged periods. Vortex mixing and heating tend to facilitate the precipitation of high concentration complexes. The precipitation of cytofectin:DNA complexes represents a significant obstacle to the development of cytofectin medicines. We hypothesize that these precipitates represent a kinetic product of lipid:DNA association rather than the thermodynamically stable product which forms upon mixing at low concentration. This hypothesis follows from the following model: 1) During initial lipid:DNA binding, DNA induces lipid reorganization (polynucleotide coating), resulting in DNA condensation and/or particle restructuring (complex maturation-formation of the thermodynamic product). There are energetic barriers to such restructuring which reflect lipid:lipid interactions, displacement of the counterion during polynucleotide binding, lipid:polynucleotide binding, and alterations in polynucleotide hydration during condensation. Therefore, the rate of such reorganization will be a function of lipid structure, counterion type, polynucleotide structure, and temperature. 2) Partially reorganized complexes are subject to aggregation upon collision in solution. This aggregation (e.g. cross linked protocomplexes- a kinetic product) may be mediated via binding of uncoated polynucleotide by uncomplexed cytofectin present on the surface of the colliding particle. Therefore, we predict that aggregation will be a function of concentration, system energy (temperature, vortexing), solution viscosity, and time.

For Table 3, the dynamic light scattering (DLS) estimates of sonicated versus unsonicated DNA-lipid complexes were for increasing plasmid DNA concentrations at a fixed 2:1 lipid-DNA charge ratio. Sizing experiments were designed to mimic murine lung transfection conditions. The complex was sonicated briefly (30" to 2 minutes) using a bath sonicator (Laboratory equipment, Hicksville NY or the equivalent) at 56° C. (above the phase transition temperature of the lipoyl moieties within the cytofectin) until visible aggregates were dispersed. DLS experiments were performed using a Brookhaven Instruments BI-90 particle sizer, or the equivalent, at 25° C., sampled continuously for five minutes and analyzed by the methods of cumulants. No significant shift in particle size distribution was observed over time (data not shown).

TABLE 3

Effect of Formulation with Heating and Sonication on Cytofectin: DNA Particle Size.

| [DNA] mg/ml | Sonicated | | Unsonicated | |
|---|---|---|---|---|
| | effective diameter | polydispersity index | effective diameter | polydispersity index |
| 0.1 | 400 | 0.268 | 3900 | 1.548 |
| 0.2 | 300 | 0.019 | 2800 | 1.413 |
| 0.4 | 288 | 0.092 | 5700 | 3.682 |
| 0.8 | 334 | 0.154 | 2268 | 2.094 |
| 1.0 | 929 | 0.685 | 2110 | 1.800 |

Methods for overcoming the aggregation and precipitation of high concentration complexes would greatly facilitate preparation of cytofectin-based genetic medicines. Unfortunately, adding thermal energy would be predicted to both facilitate "maturation" and to increase diffusion within the system, thereby increasing collision rate and energy. We hypothesize that heating combined with either an increase in system viscosity or use of sonication to rapidly resolve aggregates prior to restructuring and precipitation will favor formation of the thermodynamic product. As demonstrated in Table 3 above, the combination of heating with sonication does result in the formation of stable, smaller lipidic particles. Furthermore, this process appears to enhance the pulmonary transfection activity of a range of lipids (see FIG. 12), including the relatively inactive compound DOTAP.

EXAMPLES

Example 1

Synthesis of N,N-[Bis(2-tert-butyldiphenylsilyloxyethyl)]amine, Compound 2 in an above Specific Synthesis Scheme To a mixture of diethanolamine (4.78 g, 7.26 mmol), triethylamine (2.5 mL), and 4-dimethylaminopyridine (89 mg, 0.73 mmol) in dichloromethane (73 mL) at 0° C. was added tert-butylchlorodiphenylsilane (5.46 g, 18.14 mmol). On complete addition, the reaction mixture was allowed to warm to room temperature. After 12 h, the reaction mixture was transferred to a separatory funnel and the organic layer was washed successively with saturated aqueous sodium bicarbonate, water, and brine. The organic layer was dried (sodium sulfate), filtered, and the filtrate solvent removed in vacuo. The crude product so obtained was purified by silica gel column chromatography (1% methanol in dichloromethane) to yield 2.53 g (2.13 mmol, 29%) of 2 as an oil. $^1$H NMR (300 MHz, CDCl$_3$) d 7.70–7.34 (m, 20H), 3.79 (t, J=5 Hz, 4H), 2.79 (t, J=5 Hz, 4H), 2.09, (s, 1H), 1.05 (s, 18H); $^{13}$C NMR (75 MHz, CDCl$_3$) d 135.5, 133.6, 129.6, 127.6, 63.5, 51.7, 26.9, 19.2; IR (KBr) 3071, 2930, 1428 cm$^{-1}$.

Example 2

(±)-[(Triphenylmethoxy)methyl]oxirane, Compound 3 in an above Specific Synthesis Scheme To a mixture of (±) glycidol (4.00 g, 33.5 mmol), triethylamine (5.7 mL), and 4-dimethylaminopyridine (420 mg, 3.40 mmol) in dichloromethane (170 mL) at 0° C. was added triphenylmethyl chloride (16.5 g, 51.2 mmol). On complete addition, the reaction mixture was allowed to warm to room temperature. After 12 h, the reaction mixture was transferred to a separatory funnel and the organic layer was washed successively with saturated aqueous sodium bicarbonate, water, and brine. The organic layer was dried (sodium sulfate), filtered, and the filtrate solvent removed in vacuo. The crude product so obtained was purified by silica gel column chromatography (3% diethylether in hexane) to yield 8.70 g (27.5 mmol, 82%) of 3 as an oil. $^1$H NMR (300 MHz, CDCl$_3$) d 7.47–7.20 (m, 15H), 3.33–3.30 (m, 1 H), 3.16–3.09 (m, 3H), 2.76 (m, 1H), 2.61 (dd, J=2, 5H, 1H); $^{13}$C NMR (75 MHz, CDCl$_3$) d 143.8, 128.6, 127.9, 127.8, 127.1, 127.0, 86.7, 64.7, 51.0, 44.6; IR (KBr) 3057, 2922, 1448 cm$^{-1}$.

Example 3

(±)-3-[N,N-bis(2-tert butyldiphenylsilyloxyethyl) amino]-1-(Triphenylmethoxy)-2-propanol, Compound 4 in an above Specific Synthesis Scheme To a mixture of (±)-(triphenylmethoxy)methyloxirane (7.66 g, 24.2 mmol) and lithium perchlorate (5.87 g, 55.2 mmol) in absolute ethanol (110 mL) was added amine 2 (11.7 g, 20.2 mmol). The reaction mixture was warmed to 65° C. and allowed to stir for 24 h. After this time, the reaction solution was allowed to cool to room temperature and then transferred to a separatory funnel containing diethylether (100 mL). The resultant mixture was sequentially washed with saturated aqueous sodium bicarbonate, water, and brine. The organic layer was dried over sodium sulfate, filtered and the filtrate was concentrated by rotary evaporation to give the crude product as a yellow oil. Purification was accomplished by SiO$_2$ column chromatography (3% methanol in dichloromethane) to yield 14.5 g (16.1 mmol, 80%) of 4 as an oil. $^1$ H NMR (300 MHz, CDCl$_3$) d 7.65–7.20 (m, 25H), 3.73–3.56 (m, 5H), 3.17 (dd, J=5, 9 Hz, 1H), 2.97 (dd, J=5, 9 Hz, 1H), 2.69 (m, 5H), 2.45 (dd, J=10, 12 Hz, 1H), 1.02 (s, 18H); $^{13}$C NMR (75 MHz, CDCl$_3$) d 144.1, 135.5,134.7, 133.5, 129.6, 128.7, 128.6, 127.7, 127.6, 126.8, 86.4, 67.2, 66.1, 62.1, 58.4, 56.6, 26.8, 26.5, 19.0; IR (KBr) 3445, 3069, 2930, 1427 cm$^{-1}$.

Example 4

(±)-3-[N,N-Bis(2-tert-butyldiphenylsilyloxyethyl) amino]-1,2-propanediol, Compound 5 in an above Specific Synthesis Scheme To a mixture of amine 4 (8.43 g, 9.40 mmol) in diethylether (12 mL) was added 85% formic acid (35 mL). The resulting reaction mixture was stirred at room temperature for 20 h. After this time, solid NaHCO$_3$ was added to neutralize the acidic solution. The resultant mixture was subsequently diluted with diethylether (100 mL) and transferred to a separatory funnel. The organic layer was separated and sequentially washed with water, and brine. Purification was accomplished by SiO$_2$ column chromatography (3% methanol in dichloromethane) to yield 3.75 g (5.73 mmol, 61%) of 5 as an oil. $^1$H NMR (300 MHz, CDCl$_3$) d 7.65–7.31 (m, 20H), 3.68–3.60 (m, 6H), 3.40 (dd, J=4, 9 Hz, 1H), 2.71 (m, 4H), 2.57 (d, J=7 Hz, 2H), 1.03 (s, 18H); $^{13}$C NMR (75 MHz, CDCl$_3$) d 135.5, 133.4, 129.7, 127.7, 68.0, 64.4, 62.0, 57.2, 56.7, 26.8, 19.0; IR (KBr) 3432, 3070, 2931, 1428 cm$^{-1}$.

Example 5

(±)-3-[N, N-Bis(2-tert-butyid iphenylsilyloxyethyl) amino]1,2-bis(9(z)-octadecenoyloxy)propane, Compound 6 in an above Specific Synthesis Scheme To a mixture of diol 5 (4.78 g, 7.26 mmol), triethylamine (2.5 mL), and 4-dimethylaminopyridine (89 mg, 0.73 mmol) in dichloromethane (73 mL) at 0° C. was added dropwise oleoyl chloride (5.46 g, 18.14 mmol). On complete addition, the reaction mixture was allowed to stir at 0° C. for 4 h whereupon an additional portion of dichloromethane (20 mL) was added. The reaction mixture was then transferred to a separatory funnel and the organic layer was washed successively with saturated aqueous sodium bicarbonate, water, and brine. The organic layer was dried (sodium sulfate), filtered, and the filtrate solvent removed in vacuo. The crude product so obtained was purified by silica gel column chromatography (6% EtOAc in Hexane) to yield 2.53 g (2.13 mmol, 29%) of 6 as an oil. $^1$H NMR (300 MHz, CDCl$_3$) d 7.67–7.34 (m, 20H), 5.37 (m, 4H), 5.03 (m, 1H), 4.29 (dd, J=3, 12 Hz, 1H), 4.06 (dd, J=6, 12 Hz, 1H), 3.65 (t, J=6, 4H), 2.67 (m, 6H), 2.23 (m, 4H), 2.02 (m, 8H), 1.51 (m, 4H), 1.29 (m, 40), 1.05 (s, 18H), 0.90 (t, J=5 Hz, 6H); $^{13}$C NMR (75 MHz, CDCl$_3$) d 173.3, 172.9, 135.5, 133.6, 130.0, 129.8, 129.7, 129.6, 127.6, 127.5, 70.0, 63.5, 62.5, 57.0, 55.4, 34.3, 34.05, 31.9, 30.0, 29.8, 29.7, 29.5, 29.4, 29.3, 29.2, 29.1 (2), 27.4, 27.2, 27.0, 26.8, 24.9 (2), 22.7, 19.1, 14.1; IR (KBr) 3071, 2927, 1741 cm$^{-1}$.

Example 6

(±)-3-[N,N-Bis(2-hydroxyethyl)amino]-1,2-bis(9(z) octadecenoyloxy)propane, Compound 7 in an above Specific Synthesis Scheme To a solution of amine 6 (2.50 g, 2.10 mmol) in THF (11 mL) at 0° C. was added dropwise a solution of tetrabutylammonium fluoride (6 mL of a 1M solution in THF, 6 mmol). The reaction was stirred at 0° C. for 15 h at which time analysis by thin layer chromatography revealed that no starting material was present. The reaction mixture was diluted with dichloromethane and transferred to a separatory funnel. The reaction mixture was washed sequentially with saturated aqueous sodium bicarbonate, water, and brine. The resultant organic layer was dried over sodium sulfate, filtered and the filtrate solvent removed in vacuo. The crude product was passed through a short column of silica gel using 5% methanol in methylene chloride to yield 1.03 g (1.45 mmol, 69%) of 7 as an oil. $^1$H NMR (300 MHz, CDCl$_3$) d 5.34 (m, 4H), 5.18 (m, 1H), 4.36 (dd, J =3, 12 Hz, 1H), 4.10 (dd, J=6, 12 Hz, 1H), 3.60 (t, J=5 Hz, 4H), 2.71 (m, 6H), 2.32 (dd, J=7, 14 Hz, 4H), 2.00 (m=8H), 1.61 (m, 4H), 1.37–1.15 (m, 40H), 0.87 (t, J=6 Hz, 6H); $^{13}$C NMR (75 MHz, CDCl$_3$) d 173.7, 173.5, 129.9, 129.7, 129.6, 70.0, 63.5, 59.8, 57.2, 55.8, 34.3, 34.0, 31.9, 29.7 (2), 29.6 (2), 29.5, 29.4, 29.3, 29.1 (2), 27.2, 27.1, 24.8, 22.6, 14.1; IR (KBr) 3416, 2925, 1740 cm$^{-1}$.

Example 7

(±)-N,N-[Bis(2-hydroxyethyl)]-N-methyl-N-[2,3-bis (9(z)-octadecenoyloxy)propyl]ammonium chloride (DODHP), Compound 1 in an above Specific Synthesis Scheme To a sealed tube containing amine 7 (0.40 g, 0.56 mmol) was added iodomethane (3 mL). The tube was flushed with argon then sealed. The reaction mixture was heated to 80° C. for 15 h. After this time, the reaction mixture was concentrated under a stream of argon (Caution: perform evaporation in a fume hood). The resulting yellow oil was dissolved in methylene chloride and transferred to a round bottomed flask. This mixture was concentrated by rotary evaporation to insure that all residual iodomethane was removed. The crude product was passed through a short silica gel column (gradient, 5%–10% methanol in dichloromethane) to yield 0.47g (0.55 mmol, 98%) of 1 as a wax. $^1$H NMR (300 MHz, CDCl$_3$) d 5.69 (m, 1H), 5.32 (m, 4H), 4.47 (dd, J=3, 12 Hz, 1H), 4.25–4.12 (m, 5H), 3.95–3.76 (m, 6H), 3.36 (s, 3H), 2.57 (s, 2H), 2.37 (m, 4), 1.99 (m, 8H), 1.58 (m, 4H), 1.37–1.24 (m, 40H), 0.86 (t, J=6 Hz, 6H); $^{13}$C NMR (75 MHz, CDCl$_3$) d 173.2, 172.7, 129.9, 129.5 (2), 65.5 (2), 63.9, 63.3, 55.6, 51.2, 34.2, 33.9, 31.8, 29.7, 29.5, 29.4, 29.2, 29.1, 29.0 (2), 27.1, 24.7, 24.6, 22.6, 14.0); IR (KBr).

Example 8

(±)-1-(Triphenylmethoxy)-3-[N N-bis(2-methoxyethyl)amino]-2-propanol, Compound 10 in an above Specific Synthesis Scheme To a mixture of oxirane 3 (5.00 g, 15.8 mmol) and lithium perchlorate (3.36 g, 31.6 mmol) in absolute ethanol (80 mL) was added amine 9 (2.53 g, 19.0 mmol). The reaction mixture was warmed to 65° C. and allowed to stir for 24 h. After this time, the reaction solution was allowed to cool to room temperature and then transferred to a separatory funnel containing diethylether (20 mL). The resultant mixture was sequentially washed with saturated aqueous sodium bicarbonate, water, and brine. The organic layer was dried over sodium sulfate, filtered and the filtrate was concentrated by rotary evaporation to give the crude product as a yellow oil. Purification was accomplished by SiO$_2$ column chromatography (3% methanol in dichloromethane) to yield 6.46 g (14.18 mmol, 90%) of 10 as an oil. $^1$H NMR (300 MHz, CDCl$_3$) d 7.49–7.22 (m, 15H), 3.82 (m,1H), 3.44 (m, 4H), 3.34 (s, 6H), 3.22 (dd, J=6, 9 Hz, 1H), 3.06 (dd, J=6, 9 Hz,1H), 2.89–2.71 (m, 5H), 2.57 (dd, J=9, 13 Hz, 1H); $^{13}$C NMR (75 MHz, CDCl$_3$) d 144.0, 128.7, 127.7, 126.9, 71.2, 67.8, 66.0, 58.7, 58.4, 54.7; IR (KBr) 3437, 3058, 2874, 1449 cm$^{-1}$.

Example 9

(±)-3-[N,N-Bis(2-methoxyethyl)amino]-1,2-propanediol, Compound 11 in an above Specific Synthesis Scheme To a mixture of amine 10 (2.86 g, 6.28 mmol) in diethylether (13.4 mL) was added 85% formic acid (16.7 mL). The resulting reaction mixture was stirred at room temperature for 20 h. After this time, NaHCO$_3$ was added to neutralize the acidic solution. The resultant mixture was subsequently diluted with diethylether () and transferred to a separatory funnel. The organic layer was separated and sequentially washed with water, brine, and dried (sodium sulfate). Purification was accomplished by SiO$_2$ column chromatography (3% methanol in dichloromethane) to yield 0.99 g (4.64 mmol, 74%) of 11 as an oil. $^1$H NMR (300 MHz, CDCl$_3$) d 3.68 (m, 2H), 3.53–3.39 (m, 6H), 3.33 (s, 6H), 2.86–2.70 (m, 5H), 2.64 (d, J=6 Hz, 2H); $^{13}$C NMR (75 MHz, CDCl$_3$) d 71.1, 68.7, 64.7, 58.7, 57.7, 54.8; IR (KBr) 3413, 2876 cm$^{-1}$.

Example 10

(±)-3-[N,N-Bis(2-methoxyethyl)amino]-1,2-bis(9(z)-octadecenoyloxy)propane, Compound 12 in an above Specific Synthesis Scheme To a mixture of diol 11 (0.30 g, 1.41 mmol), triethylamine (0.5 mL), and 4-dimethylaminopyridine (17.2 mg, 0.14 mmol) in dichloromethane (14 mL) at 0° C. was added dropwise oleoyl chloride (1.10 g, 3.66 mmol). On complete addition, the reaction mixture was allowed to stir at 0° C. for 4 h whereupon an additional portion of dichloromethane (10 mL) was added. The reaction mixture was then transferred to a separatory funnel and the organic layer was washed successively with saturated aqueous sodium bicarbonate, water, and brine. The organic layer was dried (sodium sulfate), filtered, and the filtrate solvent removed in vacuo. The crude product so obtained was purified by silica gel column chromatography (1% methanol in dichloromethane) to yield 150 mg (0.21 mmol, 15%) of 12 as an oil. $^1$H NMR (300 MHz, CDCl$_3$) d 5.31 (m, 4H), 5.08 (m, 1H), 4.35 (dd, J =3, 12 Hz, 1H), 4.09 (dd, J=6, 12 Hz, 1H), 3.40 (t, J=6 Hz, 4H), 3.29 (s, 6H), 2.76–2.68 (m, 6H), 2.26 (m, 4H), 1.98 (m, 8H), 1.58 (m, 4H), 1.35–1.22 (m, 40H), 0.85 (t, J=6 Hz, 6H); $^{13}$C NMR (75 MHz, CDCl$_3$) d 173.3, 173.0, 129.9, 129.6, 71.4, 70.1, 63.7, 58.7, 55.2. 54.8, 34.3, 34.1, 31.8, 29.7, 29.6, 29.5, 29.2, 29.1, 29.0, 27.0 (2), 24.8, 22.6,14.0; IR (KBr) 2925, 2854, 1740 cm$^{-1}$.

Example 11

(±)-N,N-Bis(2-methoxyethyl)-N-methyl-N-[2,3-bis(9(z)-octadecenoyloxy)propyl]ammonium chloride (DODMP), Compound 8 in an above Specific Synthesis Scheme To a sealed tube containing amine 12 (150 mg, 0.20 mmol) was added iodomethane (3 mL). The tube was flushed with argon then sealed. The reaction mixture was heated to 80° C. for 15 h. After this time, the reaction mixture was concentrated under a stream of argon (Caution: perform evaporation in a fume hood). The resulting yellow oil was dissolved in methylene chloride and transferred to a round bottomed flask. This mixture was concentrated by rotary evaporation to insure that all residual iodomethane was removed. The crude product was passed through a short silica gel column (gradient, 5%–10% methanol in dichloromethane) to yield 162 mg (0.19 mmol, 95%) of 8 as a wax. $^1$H NMR (300 MHz, CDCl$_3$) d 5.59 (m, 1H), 5.24 (m, 4H), 4.40 (dd, J=3, 12 Hz, 1H), 4.13–3.75 (m, 11H), 3.34 (m, 9H), 2.25 (m, 4H), 1.91 (m, 8H), 1.51 (m, 4H), 1.27–1.15 (m, 40H), 0.78 (m, 6H); $^{13}$C NMR (75 MHz, CDCl$_3$) d 172.8, 172.6, 129.8, 129.4, 129.4, 65.9 (2), 63.5, 63.2, 63.0, 59.2, 50.4, 34.1, 33.8, 31.7, 29.5 (2), 29.3, 29.2 (2), 29.1, 29.0, 28.9 (2), 29.8, 27.0 (2), 24.5, 24.4, 22.5, 13.9; IR (KBr) 3004, 2925, 1744 cm$^{-1}$.

Example 12

(±)-N-(2,2,2-Trifluoroethyl)-N,N-dimethyl-N-[2,3-bis(9(z)-octadecenyloxy)propyl]ammonium chloride (DOFEP), Compound 14 in an above Specific Synthesis Scheme To a sealed tube containing amine 15 (0.50 g, 0.77 mmol) in DMF (5 mL) was added 2-iodo-1,1,1-trifluoroethane (1.1 mL). The tube was flushed with argon then sealed. The reaction mixture was heated to 100° C. for 15 h. After this time, the reaction mixture was transferred round bottom flask and the volatiles (DMF, excess ICH$_2$CF$_3$) were removed via distillation at reduced pressure. The resulting yellow oil was passed through a short silica gel column (gradient, 5%–10% methanol in dichloromethane) to yield 67 mg (0.07 mmol, 10%) of 14 as a solid. $^1$H NMR (300 MHz, CDCl$_3$) d 5.59 (m, 1H), 5.33 (m, 4H), 4.51 (m, 2H), 4.13 (dd, J=6, 12, 1H), 3.87 (dd, J=9, 14 Hz, 1H), 3.53 (s, 6H), 2.35 (m, 4H), 1.99, (m, 8H), 1.59 (m, 4H), 1.29–1.25 (m, 40H), 0.87 (t, J=7 Hz, 6H);; $^{13}$C NMR (75 MHz, CDCl$_3$) d 173.0, 172.5, 129.9, 129.8, 129.5, 129.4, 66.0, 65.6, 62.8, 54.6, 34.1, 33.8, 31.7, 39.7, 29.6, 29.4 (2), 29.3, 29.1 (2), 29.0 (2), 28.9, 27.1, 27.0, 24.6, 2.45, 22.5, 13.9); IR (KBr).

Example 13

Liposome Formulation

An appropriate mass of the cationic lipid and a neutral lipid (DOPE) were added as solutions in chloroform to 1.9 mL sample vials to yield a 50:50 molar ratio of cationic lipid:neutral lipid. The chloroform was removed via rotary evaporation at 37° C. The resulting thin lipid films were placed under vacuum overnight to insure that all traces of solvent have been removed. The lipid mixture was resuspended in 1 mL sterile water at 70° C. until the film is hydrated, and then vortex mixed to afford an emulsion (unsonicated preparation). These emulsions were formulated at a cationic lipid concentration of 1 mM. To form the sonicated preparations used in this study, the lipid emulsions were sonicated using a Branson sonifier 450 sonicator equipped with a cup horn and recirculating water bath (35° C., 80% output with 2 sec delays over 15 minutes.). By performing comparative transfection experiments, it was determined that sonication of cytofectin emulsions above their phase transition temperature did not significantly alter transfection efficacy. Furthermore, sonication at or above 70° C. resulted in partial lipid decomposition as determined by thin layer chromatography.

Example 14

Cell Culture

NIH 3T3 cells were obtained from ATCC (CRL 1658), cultured in Dulbecco's Modified Eagle's Medium with 10% calf serum, and plated on standard 24 well tissue culture plates 12 to 24 hours prior to transfection. Cells were approximately 80% confluent at the time of transfection. CHO cells (ATCC CCL 61) were cultured using Ham's F12 medium supplemented with 10% fetal calf serum, and plated as described for NIH 3T3.

Example 15

Transfection of Cultured Cells

NIH 3T3 cells were plated onto 24 well tissue culture plates as described above. The growth media was removed via aspiration and the cells were washed once with 0.5 mL PBS/well. The liposome/DNA complexes were formed through sequential addition of appropriate amounts of DMEM (serum-free), plasmid DNA (4 micrograms), and the liposome formulation into a 2 mL Eppendorf tube to a total volume of 800 microliters. Typically, 24 microliters of a lipid emulsion (1 mM cytofectin, 1 mM DOPE) were used to complex 4 micrograms of DNA to yield a 2:1 cytofectin to DNA molar charge ratio. The addition of these substances was followed by thorough vortex mixing and incubation for 15 minutes at room temperature. A 200 microliter aliquot of the resultant transfection complex was added to each well (1 microgram DNA/well, n=4) and the cells were incubated for 4 hrs. at 37° C. At this time, 500 microliters of the appropriate growth media +10% calf serum/well was added and the cells cultured for approximately 48 hours prior to lysis and analysis. The sample transfections were subsequently repeated a minimum of three times for each cell line in order to ensure reproducibility.

Example 16

Intratracheal Instillation of DNA or Lipid/DNA Complexes

Female Balb/C mice (specific pathogen free) weighing approximately 20 to 21 grams were obtained from Charles River Laboratories. Anesthesia was provided for invasive procedures and animals were terminated by $CO_2$ inhalation in accordance with University of California, Davis guidelines. DNA was prepared for instillation by dilution in sterile water. Lipid/DNA complexes were prepared by mixing 20 micrograms of plasmid DNA (Luciferase) at a 4:1 molar charge ratio (cationic lipid:DNA) in sterile water for injection (total volume of 240 microliters). Mixtures were prepared and vortex mixed at room temperature, and injected within 5 minutes of lipid:DNA complex formation. Neck dissections were performed on anesthetized mice using a 1 cm incision through the skin of the anterior neck, dissection of the salivary gland and musculature surrounding the anterior trachea immediately below the larynx, and instillation of 240 microliters of DNA or lipid/DNA complex using a ½" 30 g needle inserted 1–3 tracheal ring interspaces inferior to the larynx. After injection, the salivary gland was placed over the tracheal defect, and the superficial neck wound closed with staples. Mice were killed 48 hours after treatment and a tracheal/lung block dissected, homogenized in lysis buffer, and assayed for luciferase protein as described below. Mock treated mouse lung/trachea was used for assessment of background luciferase activity. No activity was detected in control mock-treated mouse tissue.

Example 17

Luciferase Assay

Relative luciferase activity was determined by using the Enhanced Luciferase Assay Kit and a Monolight 2010 luminometer (both from Analytical Luminescence Laboratories, San Diego, Calif.). This was accomplished by directly applying 233.3 mL of concentrated luciferase lysis buffer (final concentration 0.1M potassium phosphate pH 7.8, 1% Triton X100, 1 mM DTT, 2 mM EDTA) to each well and placing the cells on ice for 15 minutes. Removal of growth media was not necessary prior to the application of the lysis buffer. This technique enhances reproducibility by avoiding the possibility of cell loss during media removal. An analogous experiment where the growth media was removed afforded similar results. Luciferase light emissions from 31 mL of the lysate were measured over a 10 second period, and results were expressed as a function of an assumed total lysate volume of 933.3 mL. Activity has been expressed as relative light units, which are a function of assay conditions, luciferase concentration, luminometer photomultiplier tube sensitivity and background. Under the conditions described above, relative light units are related to luciferase protein mass by the equation [fg luciferase=(RLU/ 48.6) -824].

Example 18

Generation of Counterion Species

A panel of DOTAP analogs was prepared by altering the anionic counterion that accompanies the ammonium head group using ion-exchange chromatography. N-(1-(2,3-Dioleoyloxy)propyl)-N,N,N-trimethylammonium iodide (DOTAP) was prepared in a similar manner to the Silivius method (Leventis, R. and Silvius, J. R. (1990) Fiochim. Biophys. Acta 1023, 124–132). Chloride substitution was achieved using Dowex strongly anionic exchange resin, 8% crosslink (200–400 mesh), chloride form. Acetate substitution was performed using the anionic exchange resin AG1-8X (200-4-mesh), acetate form, and the remaining counterions were obtained using the hydroxide form of this resin. The chloride and acetate ion exchange was performed by suspending the corresponding resin (1.0–1.5 g) in highly purified filtered water (10–20 ml), and loading into a narrow bore glass column. The column was washed with water (5×, 5 ml), methanol (10×, 5 ml), and equilibrated with a CH$_3$OH—CH$_2$Cl$_2$ (8:2) solution. A solution of the cationic lipid (50–70 mg lipid in ca. 1 ml CH$_3$OH—CH$_2$Cl$_2$ (8:2)) was then gravity eluted through the column. For the substitution of all other counterions, the hydroxide resin was pretreated by washing with a 1M solution of the desired counterion as its sodium salt. The loaded resin was then washed with water until the eluent pH stabilized at approximately 7. The ion exchange chromatography was then performed using the CH$_3$OH—CH$_2$Cl$_2$ equilibration sequence described above. Electrospray ionization mass spectrometry was used to verify the composition of the resulting salt forms.

The influence of these counterions on transfection was studied by using lipid films and lipid-DNA complexes that were prepared, transfected, and subsequently analyzed as previously described (Ruysschaert, J. M., el Ouahabi, A., Willeaume, V., Huez, G., Fuks, R., Vandenbranden, M. and Di Stefano, P. 1994. A novel cationic amphiphile for transfection of mammalian cells. Biochem. Biophys. Res. Commun. 203(3): 1622–8). The plasmid pNDCLux, which encodes the *P. pyralis* luciferase, was Example 19

Transfection Data

Interpretation of the various figures is facilitated by reference to the above described compounds and to the following list of abbreviations, prefixes, or suffixes and the associated structures:

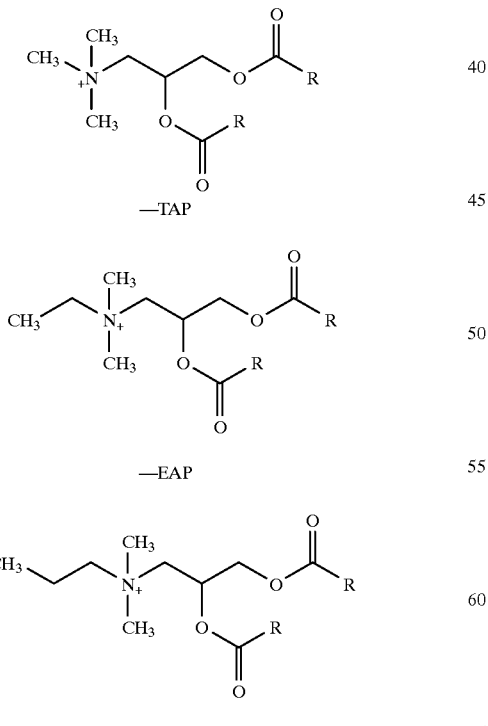

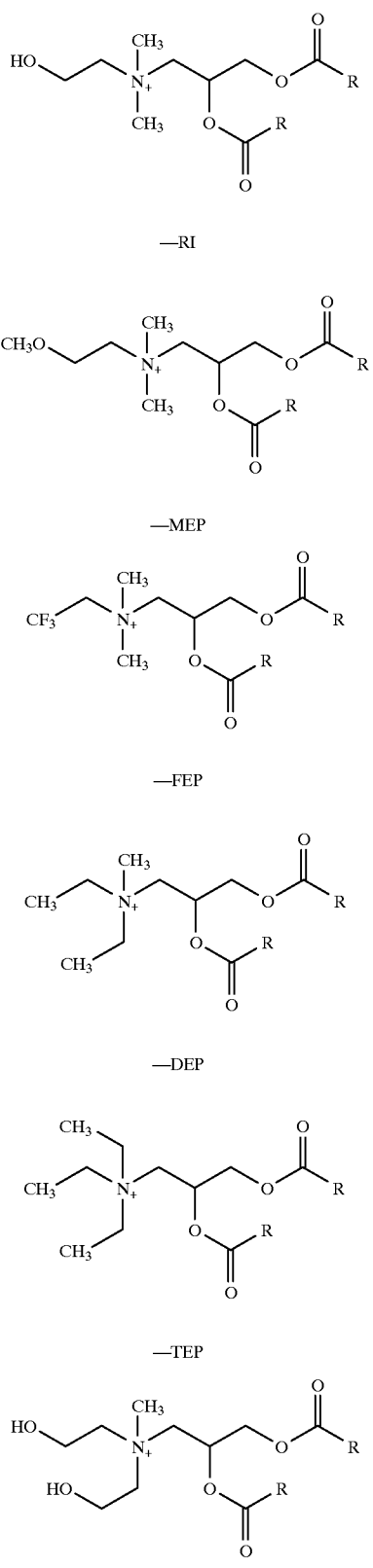

-continued

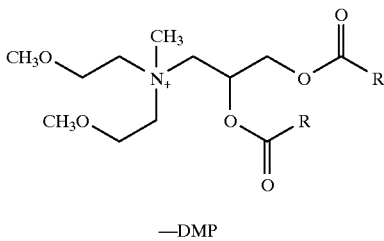

—DMP

| DO | as a prefix for the above "R" indicates dioleoyl (with the carbonyl) |
| DM | as a prefix for the above "R" indicated dimyristoyl (with the carbonyl) |
| DOPE | Dioleoylphosphatidylethanolamine |
| DOTMA | N-[1-(2,3-dioleyloxy)propyl]-N,N,N-trimethylammonium bromide [DIETHER] |

FIG. 1 shows a comparison of cytofectin-mediated DNA transfection using NIH 3T3 cells. DNA transfections were performed in quadruplicate as described in the experimental procedures using a 2:1 molar charge ratio (lipid charge to DNA phosphate charge). The data demonstrates that the incorporation of a dihydroxyethyl substituted ammonium functionality in the lipid polar domain leads to significantly higher transfection efficacy in vitro. Results are summarized in bar graph form as the mean (n=4) and standard deviation of total luciferase light units (RLU) obtained from cells lysed after transfection of 1 microgram of DNA. All cytofectins were formulated at a 1:1 molar ratio with DOPE.

Figure 2:
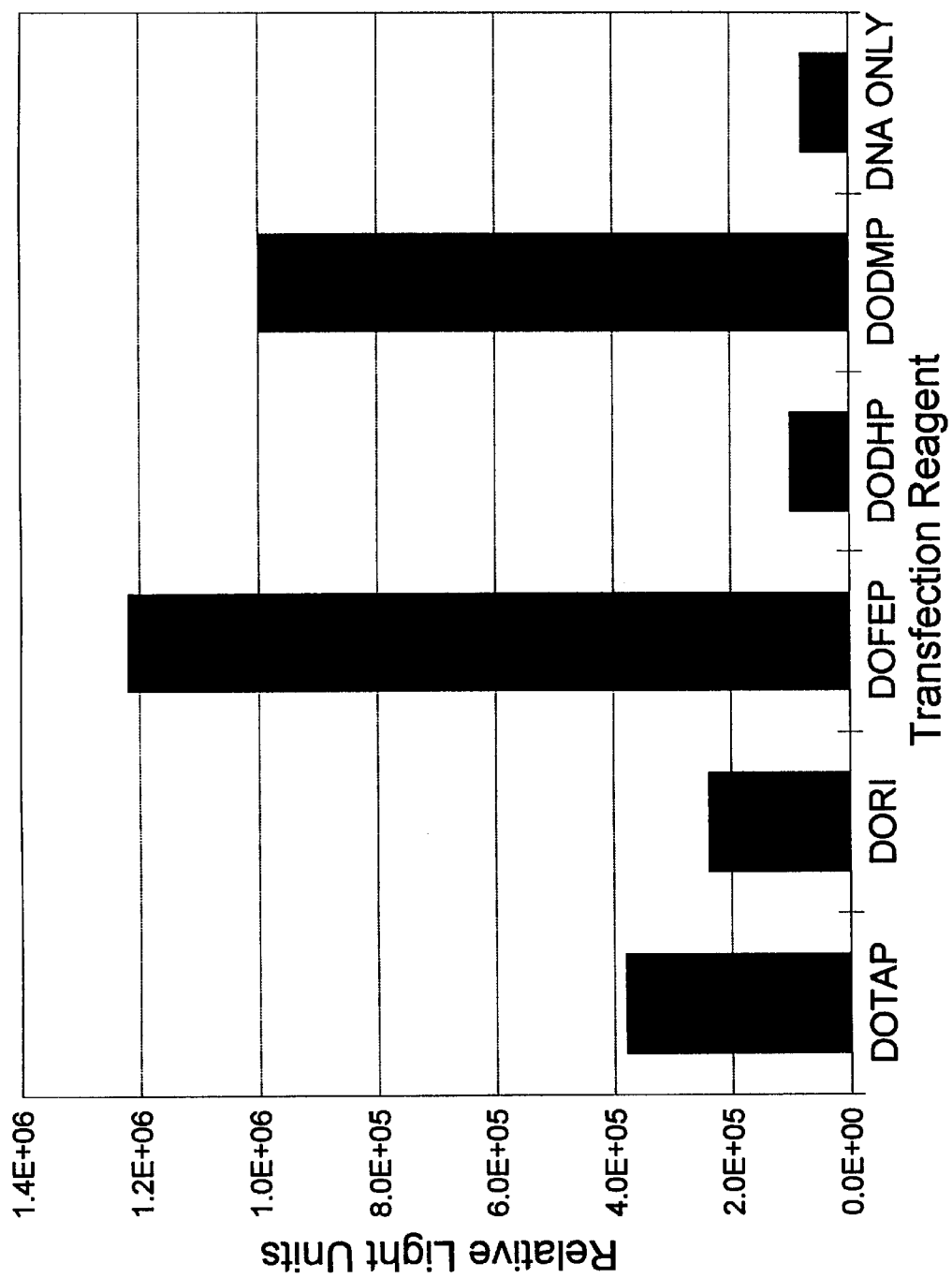
FIG. 2 presents an in vivo comparison of cytofectin-mediated DNA transfection in Balb-C mice.

In FIG. 2 there is shown an in vivo comparison of cytofectin-mediated DNA transfection. Balb-C mice were transfected with plasmid DNA using various cytofectins. Intratracheal instillations of cytofectin:DNA complexes were performed as described in the experimental procedures. The data demonstrates that the incorporation of dimethoxyethyl and triflouroethyl substituted ammonium functionality in the lipid polar domain leads to significantly higher transfection efficacy in vivo. Results are summarized in bar graph form as the mean (n=4) and standard deviation of total luciferase light units (RLU) obtained from trachea/lung blocks lysed 48 hours after treatment with 20 micrograms of DNA.

Figure 3:
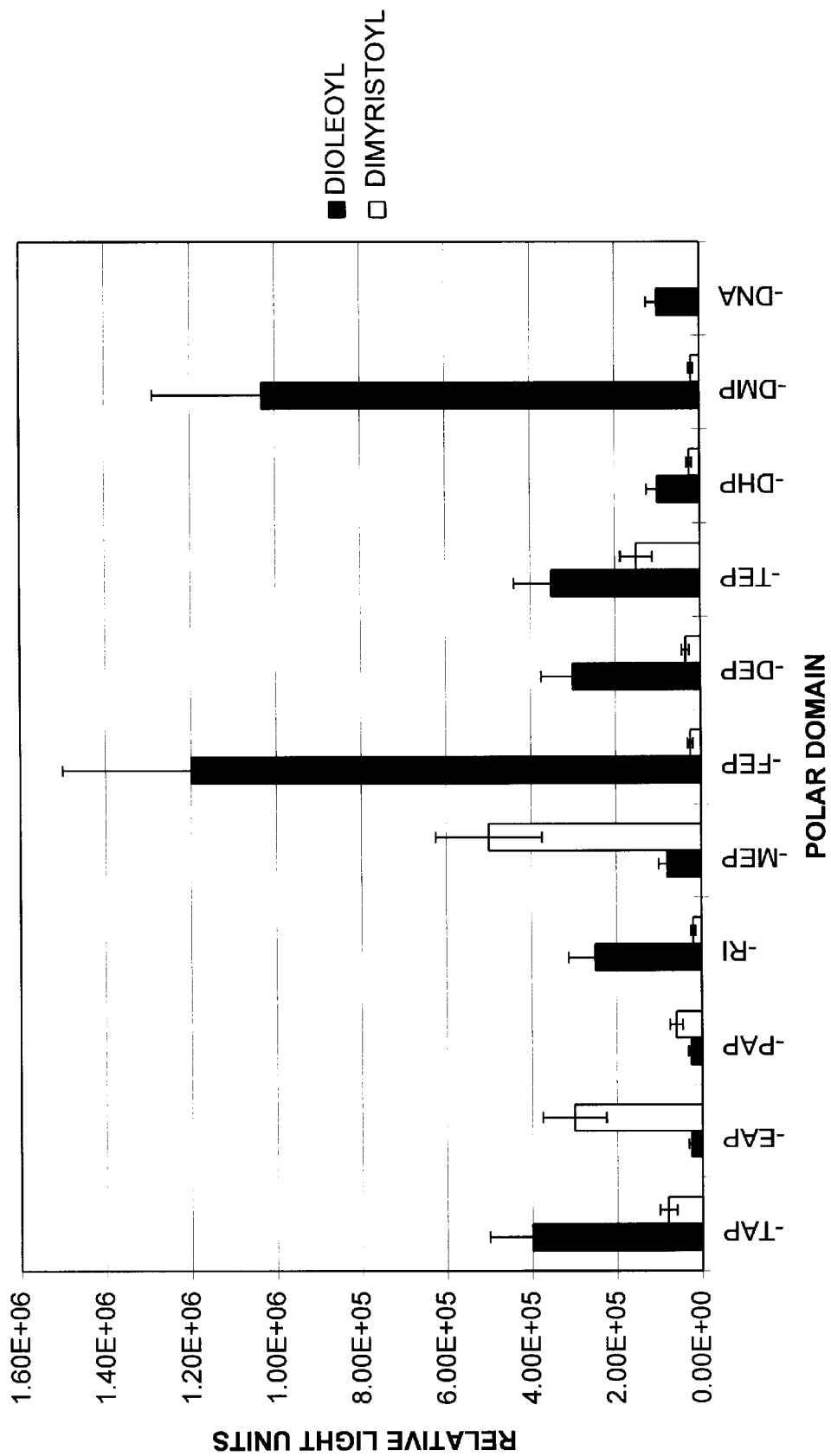
FIG. 3 shows transfection in vivo data for various amine cytofectins.
Figure 4:
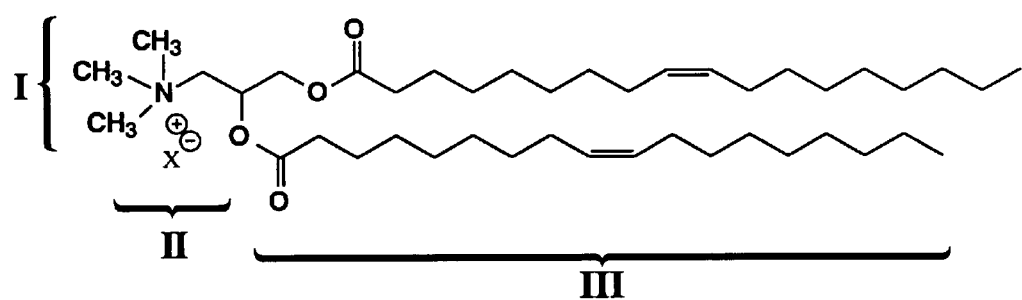
FIG. 4 shows the identification of cytofectin structural domains.

The transfection activity of various compounds is illustrated in FIG. 3. As can be seen in FIG. 3, the dioleoyl derivatives of –FEP and DMP of the subject invention are exceptionally effective in transfection. General transfection conditions were as above.

Figure 6:
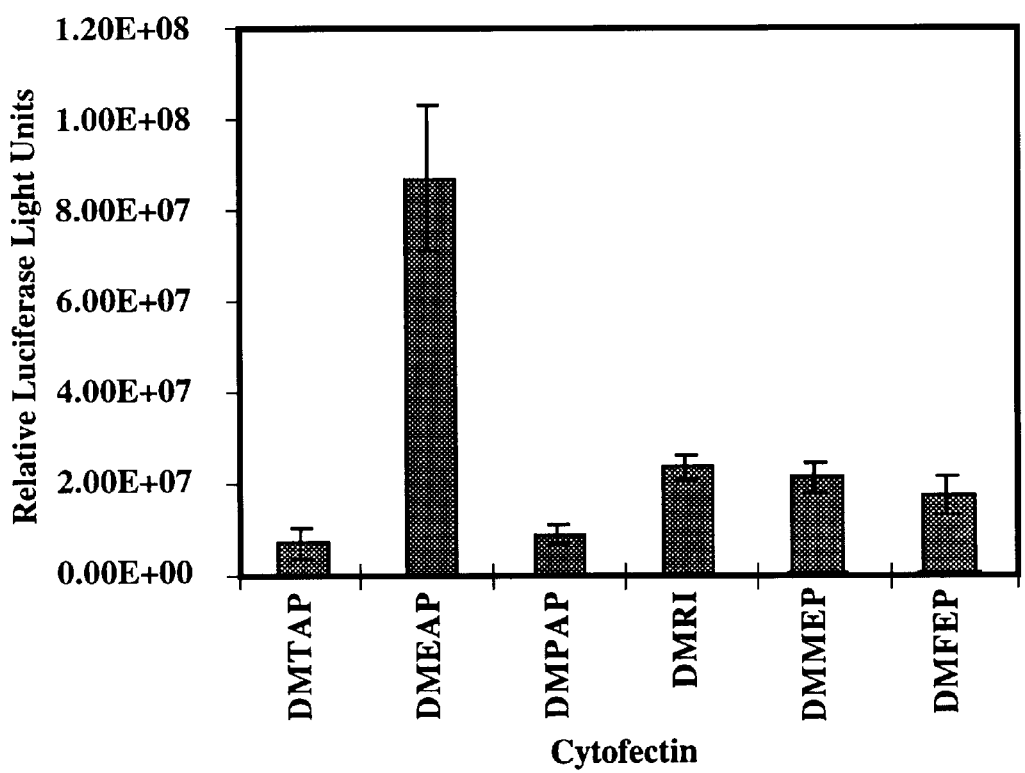
FIG. 6 shows a comparison of cytofectin polar domain structure to transfection activity in NIH 3T3 cells.
Figure 5:
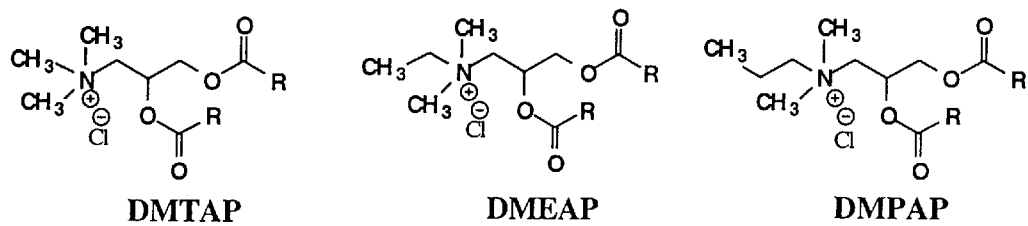
FIG. 5; A, B, and C; shows the experimental design for polar domain analysis in which: A) illustrates an increase in cross-sectional area of the polar domain; B) shows an increase in available hydrogen bonding modes; and C) displays an increase in inductive influence on the charged center.
Figure 5:
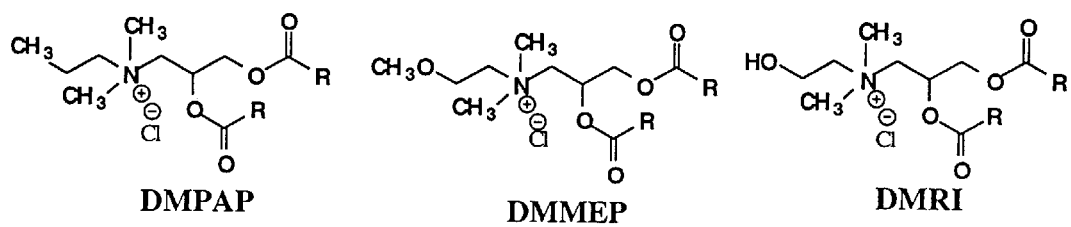
Figure 5:
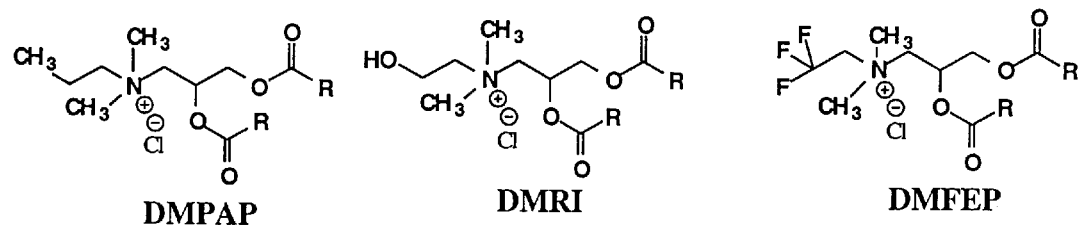

For the comparison of cytofectin polar domain structure to transfection activity in NIH 3T3 cells shown in FIG. 6, liposome formulations containing a 1:1 mole ratio of Cytofectin and DOPE were mixed with 1 mg of pNDCLUX plasmid DNA to give a 2:1 molar charge ratio (lipid charge to DNA phosphate). The resultant complex was placed directly on to the cell surface. Cell lysates obtained 48 hours after transfection were analyzed for luciferase activity. Each data point reflects the mean value of total light units derived from four transfections and the standard deviation from this mean.

Figure 7:
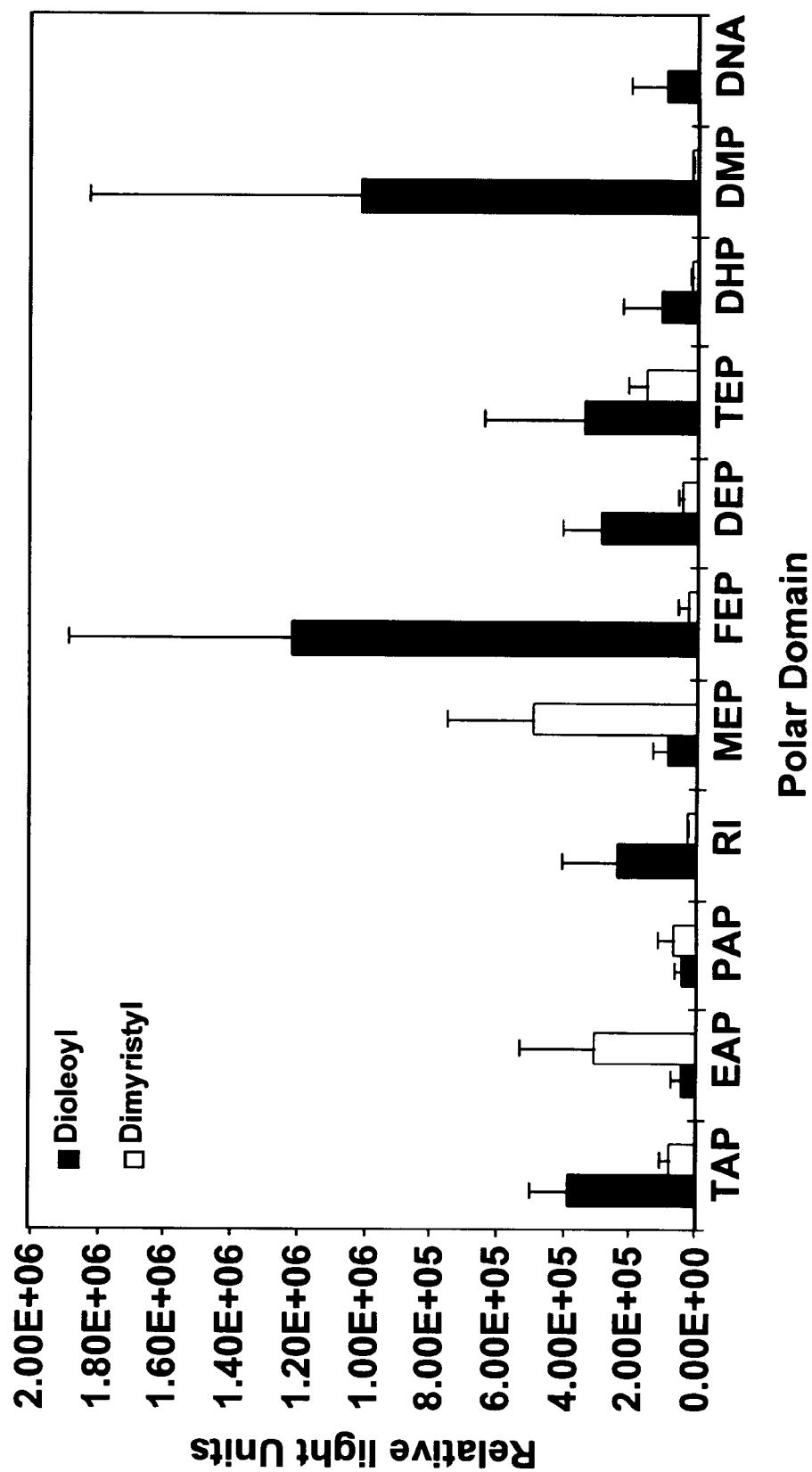
FIG. 7 shows a comparison of cytofectin polar domain structure to transfection activity in vivo for intratracheal instillation into mice with two different hydrophobic side chains.

FIG. 7 depicts intratracheal instillation into mice. For the intratracheal instillation into mice the dioleoyl hydrophobic domains are more effective than corresponding dimyristoyl analogs. Also, cytofectins incorporating inductive functionality enhance mouse intratracheal transfection.

Figure 8:
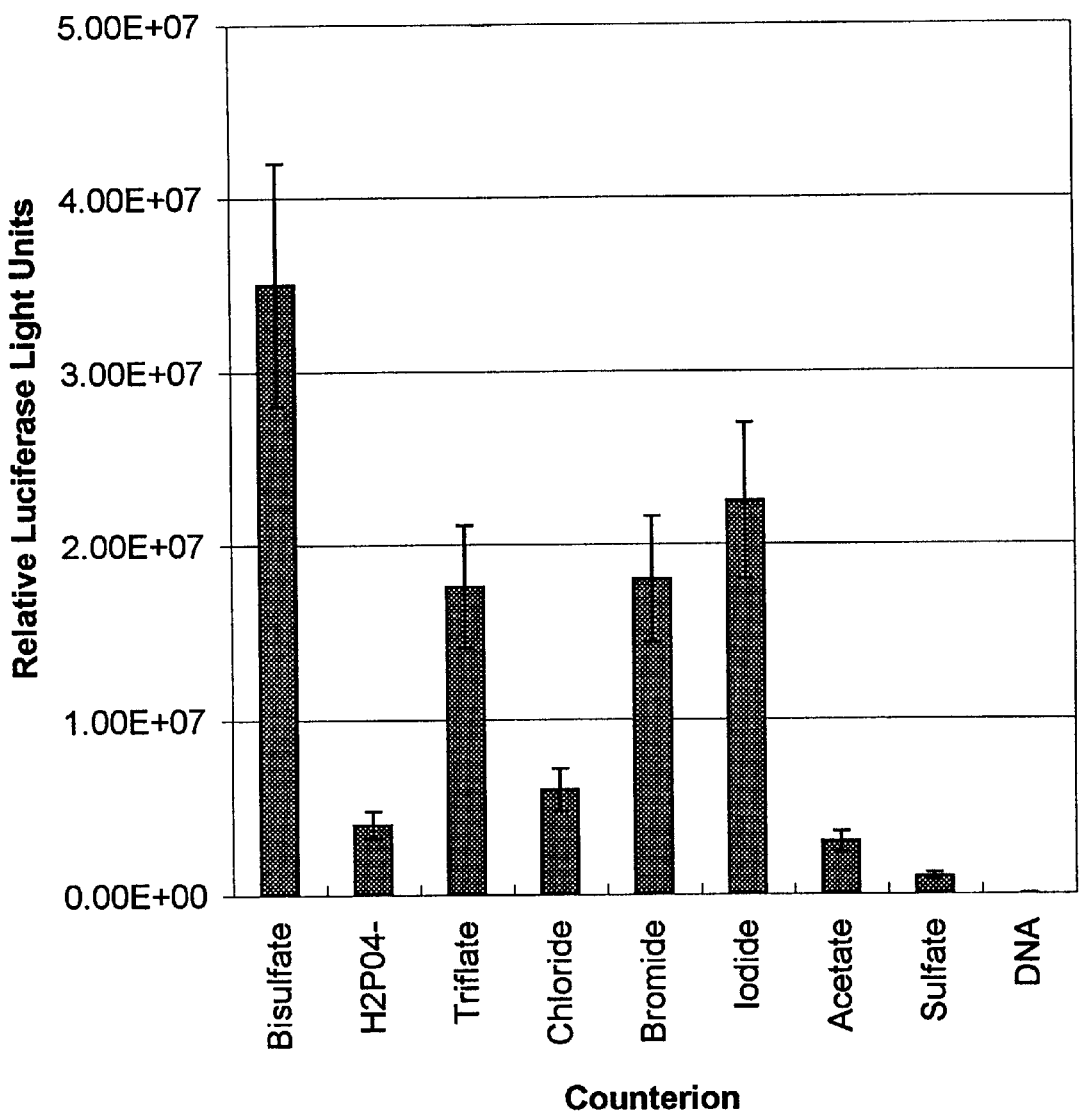
FIG. 8 shows a comparison of cytofectin counterions to transfection activity in NIH 3T3 cells.

For the comparison of cytofectin counterions to transfection activity in NIH 3T3 cells depicted in FIG. 8, liposome formulations containing a 1:1 mole ratio of Cytofectin and DOPE were mixed with 1 mg of pNDCLUX plasmid DNA to give a 2:1 molar charge ratio (lipid charge to DNA phosphate). The resultant complex was placed directly on to the cell surface. Cell lysates obtained 48 hours after transfection were analyzed for luciferase activity. Each data point reflects the mean value of total light units derived from four transfections and the standard deviation from this mean.

Figure 9:
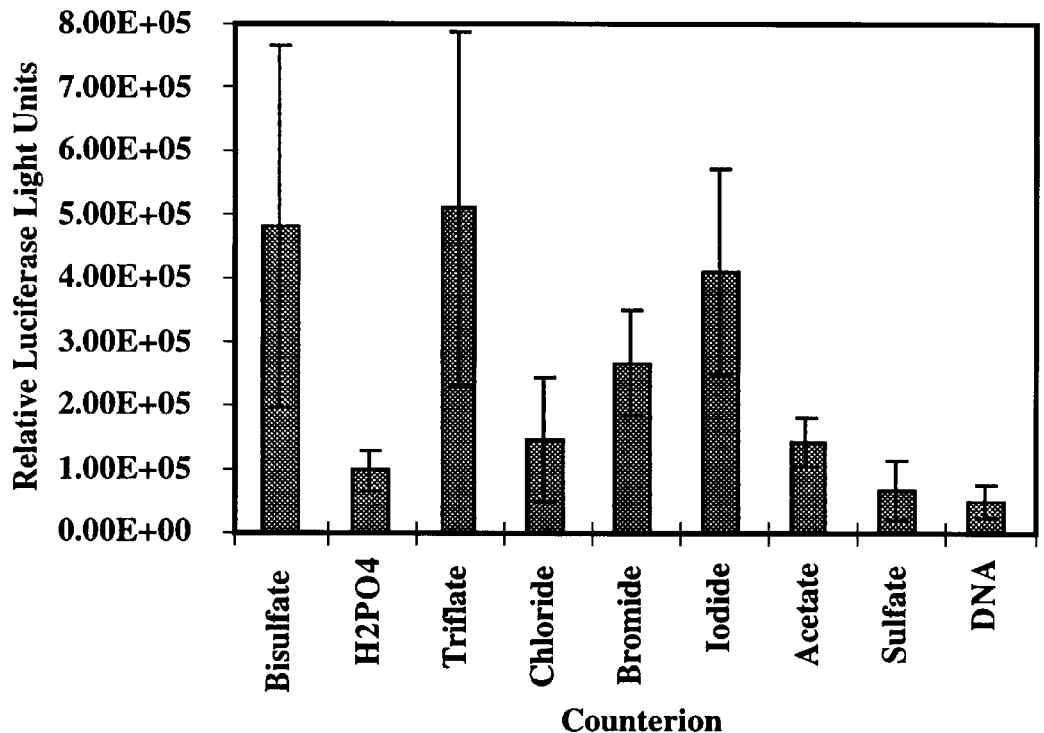
FIG. 9 shows a comparison of cytofectin counterions to in vivo transfection activity in Balb-C lung.

For the comparison of cytofectin counterions to in vivo transfection activity in Balb-C lung illustrated in FIG. 9, Balb-C mice were transfected with lipid/DNA complexes formed from mixing pNDCLUX plasmid DNA with various cytofectins (2:1 lipid to DNA phosphate charge ratio). Intratracheal installations of cytofectin:DNA complexes were performed as described elsewhere (Balasubramaniam, R. P., Bennett, M. J., Aberle, A. M., Malone, J. G., Nantz, M. H. and Malone, R. W. 1996. Structural and functional analysis of cationic transfection lipids: the hydrophobic domain. Gene Ther. 3(2): 163–172). Results are summarized in bar graph form as the mean (n=4) and standard deviation of total luciferase light units obtained from trachea/lung blocks lysed 48 hours after treatment with 20 mg of DNA.

Figure 10:
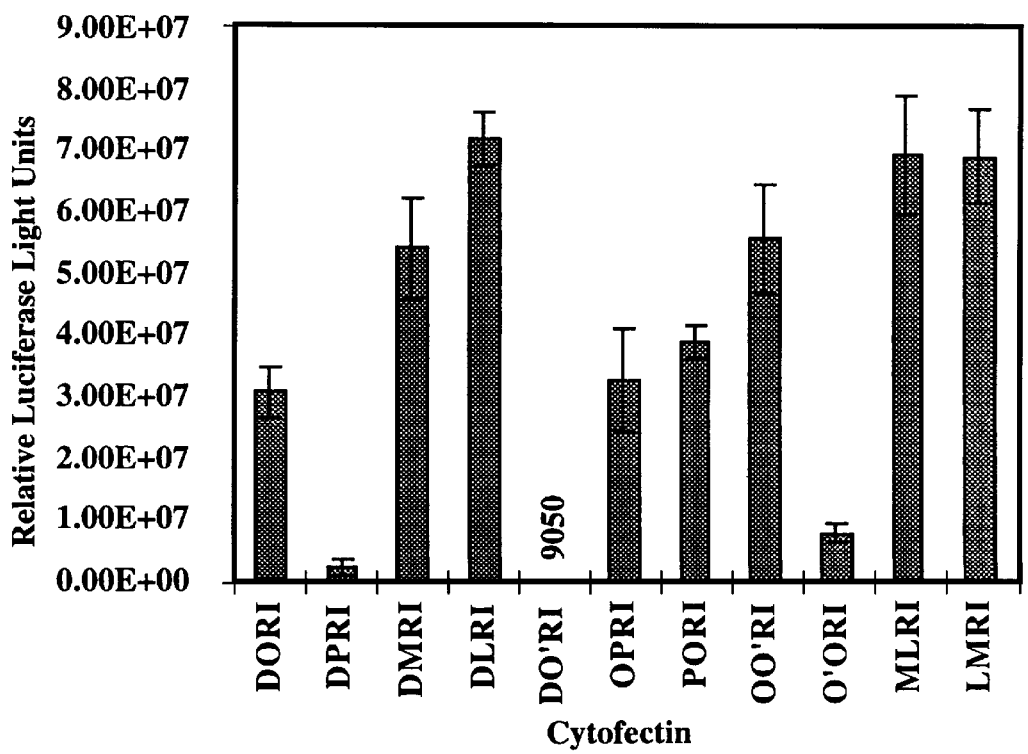
FIG. 10 shows a comparison of cytofectin hydrophobic structure to transfection activity in NIH 3T3 cells.

For the comparison of cytofectin hydrophobic structure to transfection activity in NIH 3T3 cells shown in FIG. 10, liposome formulations containing a 1:1 mole ratio of Cytofectin and DOPE were mixed with 1 mg of pCMVL plasmid DNA to give a 2:1 molar charge ratio (lipid charge to DNA phosphate). The resultant complex was placed directly on to the cell surface. Cell lysates obtained 48 hours after transfection were analyzed for luciferase activity. Each data point reflects the mean value of total light units derived from four transfections and the standard deviation from this mean.

Figure 11:
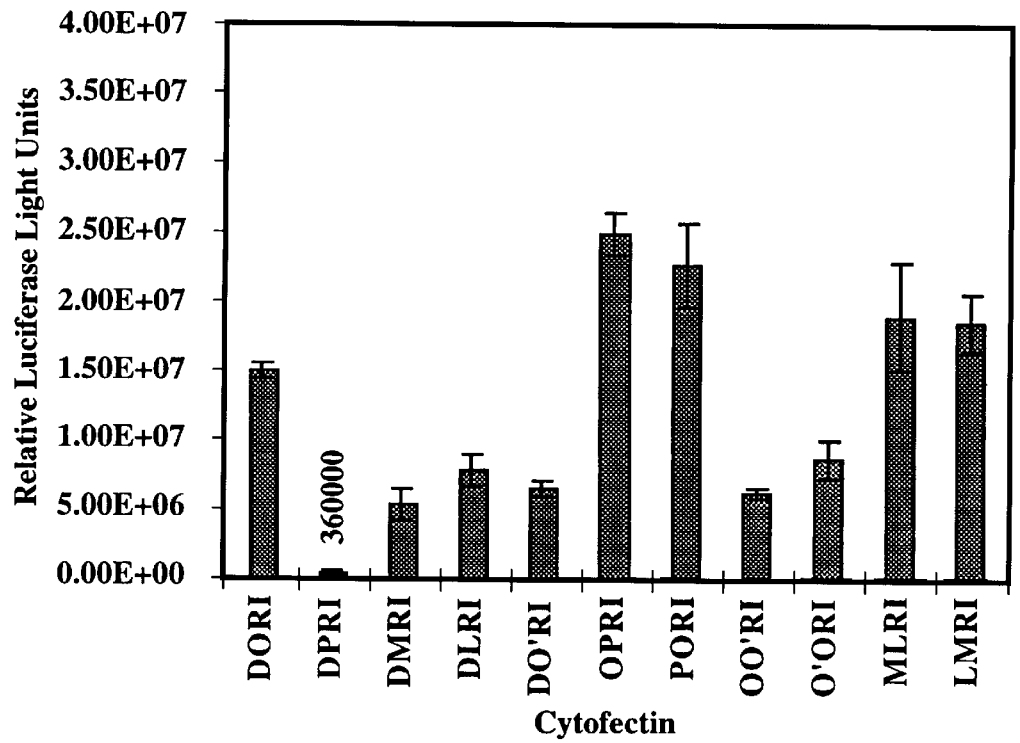
FIG. 11 shows comparison of cytofectin hydrophobic structure to transfection activity in human bronchial epithelial cells (16HBE14o-).

For the comparison of cytofectin hydrophobic structure to transfection activity in human bronchial epithelial cells (16HBE14o-) presented in FIG. 11, liposome formulations containing a 1:1 mole ratio of Cytofectin and DOPE were mixed with 1 mg of pCMVL plasmid DNA to give a 2:1 molar charge ratio (lipid charge to DNA phosphate). The resultant complex was placed directly on to the cell surface. Cell lysates obtained 48 hours after transfection were analyzed for luciferase activity. Each data point reflects the mean value of total light units derived from four transfections and the standard deviation from this mean.

Figure 12:
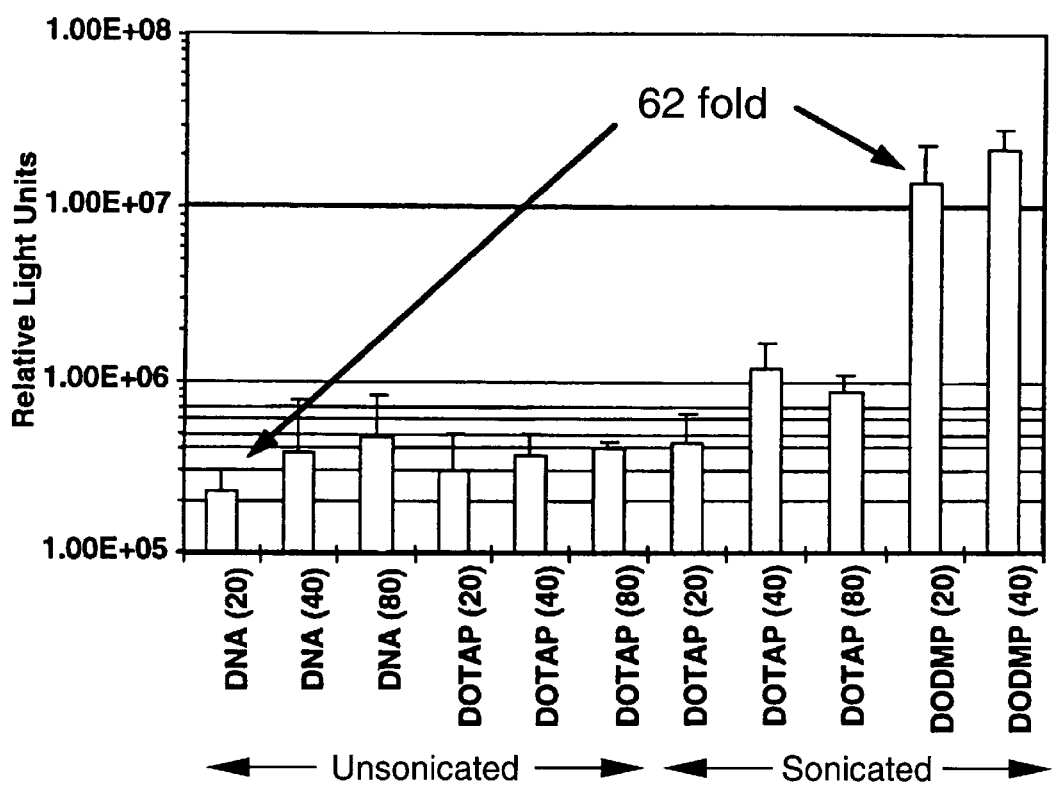
FIG. 12 shows the effects of formulation conditions on luciferase expression in murine lung.

For the effects of formulation conditions on luciferase expression in murine lung disclosed in FIG. 12, an overall increase in luciferase expression was noted for sonicated (DOTAP Bisulfate)-DNA complexes with increasing DNA concentrations at a fixed 2:1 charge ratio. Sonicated complexes were prepared as described previously (see Table 3, above). Naked DNA has been provided as a control comparison. Included are examples illustrating the effect of sonication with heating on both the active lipid DOD-MP.Chloride as well as DOTAP.Bisulfate, a widely used cationic transfection lipid.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A cytofectin:polynucleotide complex comprising:
   a) a polynucleotide and b) a cytofectin having the structure:

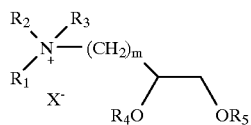

wherein m=1–10;

$R_1$ is a hydrogen, an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group;

$R_2$ is an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group $R_3$ is an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group, however, when two of $R_1$, $R_2$ and $R_3$ are alkyls or alkenyls then the other is a trihalogenated group or when $R_1$ is hydrogen and $R_2$ is an alkyl or alkenyl then $R_3$ is a trihalogenated group;

$R_4$ is an alkyl group, an alkenyl group, an alkynyl group, or an alkyl, alkenyl, or alkynyl containing acyl group;

$R_5$ is an alkyl group, an alkenyl group, an alkynyl group, or an alkyl, alkenyl, or alkynyl containing acyl group; and $X^-$ is a counterion.

2. A composition according to claim 1, wherein said counterion is selected from a group consisting of the oxyanions bisulfate or trifluoromethanesulfonate and the halides iodide or bromide.

3. A cytofectin:polynucleotide complex produced by the steps comprising:

a) mixing a cytofectin with a polynucleotide, wherein said cytofectin comprises a composition of matter having the structure:

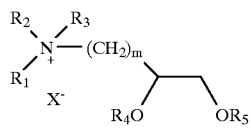

wherein m=1–10;

$R_1$ is a hydrogen, an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group;

$R_2$ is an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group $R_3$ is an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group, however, when two of $R_1$, $R_2$, and $R_3$ are alkyls or alkenyls then the other is a trihalogenated group or when $R_1$ is hydrogen and $R_2$ is an alkyl or alkenyl then $R_3$ is a trihalogenated group;

$R_4$ is an alkyl group, an alkenyl group, an alkynyl group, or an alkyl, alkenyl, or alkynyl containing acyl group;

$R_5$ is an alkyl group, an alkenyl group, an alkynyl group, or an alkyl, alkenyl, or alkynyl containing acyl group; and $X^-$ is an anion and b) energizing said mixture of cytofectin and polynucleotide for a selected period of time at a predetermined temperature to produce a thermodynamically stable product.

4. A cytofectin:polynucleotide complex produced by the steps comprising:

a) combining a cytofectin with a lipid, wherein said cytofectin comprises a composition of matter having the structure:

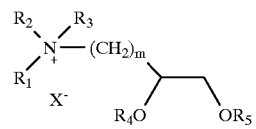

wherein m=1–10;

$R_1$ is a hydrogen, an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group;

$R_2$ is an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group $R_3$ is an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group, however, when two of $R_1$, $R_2$, and $R_3$ are alkyls or alkenyls then the other is a trihalogenated group or when $R_1$ is hydrogen and $R_2$ is an alkyl or alkenyl then $R_3$ is a trihalogenated group;

$R_4$ is an alkyl group, an alkenyl group, an alkynyl group, or an alkyl, alkenyl, or alkynyl containing acyl group;

$R_5$ is an alkyl group, an alkenyl group, an alkynyl group, or an alkyl, alkenyl, or alkynyl containing acyl group; and $X^-$ is an anion;

b) mixing said combination of cytofectin and lipid with polynucleotide; and c) sonicating said mixture of polynucleotide, cytofectin, and lipid for a selected period of time at a predetermined temperature.

5. A method for producing a transfection active cytofectin:polynucleotide complex comprising the steps:

a) combining a cytofectin having a quaternized amine and a counterion selected from a group consisting of the oxyanions bisulfate or tirfluoromethanesulfonate and the halides iodide or bromide with a lipid, wherein said cytofectin comprises a composition of matter having the structure:

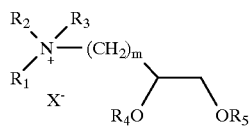

wherein m=1–10;

$R_1$ is a hydrogen, an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group;

$R_2$ is an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group $R_3$ is an alkyl group, an alkenyl group, an alkynyl group, a hydroxylated alkyl, alkenyl, or alkynyl group, an ether containing alkyl, alkenyl, or alkynyl group, or a trihalogenated alkyl, alkenyl, or alkynyl group, however, when two of $R_1$, $R_2$, and $R_3$ are alkyls or alkenyls then the other is a trihalogenated group or when $R_1$ is hydrogen and $R_2$ is an alkyl or alkenyl then $R_3$ is a trihalogenated group;

$R_4$ is an alkyl group, an alkenyl group, an alkynyl group, or an alkyl, alkenyl, or alkynyl containing acyl group;

$R_5$ is an alkyl group, an alkenyl group, an alkynyl group, or an alkyl, alkenyl, or alkynyl containing acyl group; and $X^-$ is said counterion and is selected from a group consisting of the oxyanions bisulfate or trifluoromethanesulfonate and the halides iodide or bromide;

b) mixing said combination of cytofectin and lipid with polynucleotide; and c) sonicating said mixture of polynucleotide, cytofectin, and lipid for a selected period of time at a predetermined temperature.

* * * * *